(12) United States Patent
Nakashima et al.

(10) Patent No.: US 9,724,368 B2
(45) Date of Patent: *Aug. 8, 2017

(54) UNEXTRACTED TOOTH ROOT CANAL FILLER AND DENTAL TISSUE REGENERATION METHOD FOR UNEXTRACTED TOOTH

(71) Applicant: NATIONAL CENTER FOR GERIATRICS AND GERONTOLOGY, Obu-shi, Aichi (JP)

(72) Inventors: Misako Nakashima, Obu (JP); Koichiro Iohara, Obu (JP)

(73) Assignee: NATIONAL CENTER FOR GERIATRICS AND GERONTOLOGY, Obu-Shi, Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/102,295

(22) Filed: Dec. 10, 2013

(65) Prior Publication Data

US 2014/0099605 A1    Apr. 10, 2014

Related U.S. Application Data

(62) Division of application No. 13/395,374, filed as application No. PCT/JP2010/005536 on Sep. 10, 2010, now abandoned.

(30) Foreign Application Priority Data

Sep. 11, 2009   (JP) .................................. 2009-210441

(51) Int. Cl.
A61L 27/36  (2006.01)
A61L 27/38  (2006.01)
(Continued)

(52) U.S. Cl.
CPC ................ *A61K 35/28* (2013.01); *A61C 5/50* (2017.02); *A61K 35/32* (2013.01); *A61K 38/193* (2013.01);
(Continued)

(58) Field of Classification Search
CPC ..... A61L 27/34; A61L 27/3834; A61K 35/28; A61C 5/04
(Continued)

(56) References Cited

U.S. PATENT DOCUMENTS

2003/0113812 A1   6/2003   Hemperly
2005/0079470 A1   4/2005   Rutherford et al.
(Continued)

FOREIGN PATENT DOCUMENTS

EP   2286829 A1   2/2011
JP   6-256132 A   9/1994
(Continued)

OTHER PUBLICATIONS

Jiang, Long et al. "Expression and Role of SDF-1α-CXCR4 Axis in Human Dental Pulp." Journal of endodontics 34.8 (2008): 939-944.*
(Continued)

*Primary Examiner* — Cris L Rodriguez
*Assistant Examiner* — Hao D Mai
(74) *Attorney, Agent, or Firm* — Knobbe, Martens, Olson & Bear, LLP

(57) ABSTRACT

Disclosed is a root canal filler for non-extracted tooth which causes no internal resorption or external resorption in a tooth with complete root formation, shows no odontoclast, and contributes to the regeneration of a dental tissue in which odontoblasts are smoothly aligned on the dentin wall. After pulpectomy or enlargement/cleaning of an infected root canal, a root canal filler for non-extracted tooth, which
(Continued)

comprises tooth pulp stem cells and an extracellular matrix, is inserted into the apical side of the root canal of the non-extracted tooth. The tooth pulp stem cells may be, for example, dental pulp CXCR4-positive cells. It is preferred to attach, to the crown side of the root canal, migration factor(s) including at least one factor selected from among a cell migration factor, a cell proliferation factor, a neurotrophic factor and an angiogenic factor.

8 Claims, 33 Drawing Sheets

(51) Int. Cl.
    *C12N 5/0775*   (2010.01)
    *A61K 38/19*    (2006.01)
    *A61K 35/32*    (2015.01)
    *A61C 5/50*     (2017.01)
    *A61K 35/28*    (2015.01)

(52) U.S. Cl.
    CPC ....... *A61L 27/3633* (2013.01); *A61L 27/3834* (2013.01); *A61L 27/3865* (2013.01); *C12N 5/0664* (2013.01); *A61L 2430/12* (2013.01)

(58) Field of Classification Search
    USPC ........................................................ 433/224
    See application file for complete search history.

(56) References Cited

U.S. PATENT DOCUMENTS

| | | | |
|---|---|---|---|
| 2005/0282116 | A1 | 12/2005 | Kusano |
| 2007/0248933 | A1 | 10/2007 | Rutherford et al. |
| 2009/0148486 | A1 | 6/2009 | Lu et al. |
| 2010/0196854 | A1 | 8/2010 | Shi et al. |
| 2010/0203481 | A1 | 8/2010 | Murray et al. |
| 2011/0002895 | A1* | 1/2011 | Ueda ............... A61K 35/16 424/93.7 |
| 2011/0020310 | A1 | 1/2011 | Nakashima et al. |
| 2011/0044960 | A1 | 2/2011 | Nakashima et al. |

FOREIGN PATENT DOCUMENTS

| | | | |
|---|---|---|---|
| JP | 2002-0029911 | A | 1/2002 |
| JP | 2002-363084 | A | 12/2002 |
| JP | 2004-067630 | A | 3/2004 |
| JP | 2005-263681 | A | 9/2005 |
| JP | 2006-001910 | A | 1/2006 |
| JP | 2006-211957 | A | 8/2006 |
| WO | WO 01/63287 | A1 | 8/2001 |
| WO | WO 2004/094588 | A1 | 11/2004 |
| WO | WO 2005/034789 | A2 | 4/2005 |
| WO | WO 2006/032075 | A1 | 3/2006 |
| WO | WO 2006/116530 | A2 | 11/2006 |
| WO | WO 2009/072527 | A1 | 6/2009 |
| WO | WO 2009/078971 | A1 | 6/2009 |
| WO | WO 2009/113733 | A1 | 9/2009 |
| WO | WO 2009/125859 | A1 | 10/2009 |

OTHER PUBLICATIONS

Amano, K. et al. "MMPs regulate wound healing process in rat dental pulp" Japanese Society of conservative Dentistry Magazine Oct. 5, 2007, pp. 35.
Boukpessi et al. "The effect of stromelysin-1 (MMP-3) on non-collagenous extracellular matrix proteins of demineralized dentin and the adhesive properties of restorative resins." Aug. 2008, Biomaterials, 29, 4367-4373).
Corti, S. et al. 2005 "Multipotentiality, homing properties, and pyramidal neurogenesis of CNS-derived LeX(ssea-1)+/CXCR4+stem cells" *The FASEB Journal* 19: 1860-1862.
Gotlieb, E.L. et al. 2008 "An ultrastructural investigation of tissue-engineered pulp construct implanted within endodontically treated teeth" *Journal of the American Dental Association* 139: 457-465.
Huang, G.T.-J, et al, 2009: "Stem/Progenitor Cell-Mediated De Novo Regeneration of Dental Pulp with Newly Deposited Continuous Layer of Dentin in an In Vivo Model", *Tissue Engineering*, 16(2): 605-615.
Iohara et al. "Side Population Cells Isolated from Porcine Dental Pulp Tissue with Self-Renewal and Multipotency for Dentinogenesis, Chondrogenesis, Adipogenesis, and Neurogenesis." (2006), Stem Cells, 24, 2493-2503.
Iohara, K. et al., "CD31 negative SP cells derived from dental pulp accelerate vascularization and pulp regeneration" Japanese Society of conservative Dentistry Magazine, Oct. 5, 2007, p. 106.
Iohara, et al 2007: "Development of New Pulpectomy Therapy by Regenerating Dental Pulp and Dentine, Aiming at Life Prolongation of Teeth for Aging Societies" pp. 162-166.
Ioharh, K. et al. 2008 "A novel stem cell source for vasculogenesis in ischemia: Subfraction of side population cells from dental pulp" *Stem Cells* 26: 2408-2418.
Iohara, K. et al. 2009 "Regeneration of dental pulp after pulpotomy by transplantation of CD31⁻/CD146⁻side population cells from a canine tooth" *Regenerative Medicine* 4: 377-385.
Kawanishi, H.N. et al. "Effects of an inducible nitric oxide synthase inhibitor on experimentally induced rat pulpitis" European Journal of Oral Science 2004; 112; pp. 332-327.
Koblas, T. et al. 2007 "Isolation and Characterization of Human CXCR4-Positive Pancreatic Cells" *Folia Biol (Praha)* 53: 13-22.
Kucia, M et al. 2007 "Morphological and molecular characterization of novel population of $CXCR4_+SSEA-4^+Oct-4^+$very small embryonic-like cells purified from human cord blood—preliminary report" *Leukemia* 21: 297-303.
Laureys, W. et al. 2001 "Revascularization after cryopreservation and autotransplantation of immature and mature apicoectomized teeth" *American Journal of Orthodontics and Dentofacial Orthopedics* 119: 346-352.
Moriguchi, M. et al. 1998 "Immunocytochemistry of proteoglycan in dentin and odontoblasts" *Kaibogaku Zasshi-Acta Anatomica Nipponica* 73: 239-245.
Murray, et al, 2007: "Regenerative Endodontics: A Review of Current Status and a Call for Action", *Journal of Endodontics, Lippincott Williams & Wilkins*, 33(4): 377-390.
Nakagawa, K.-I. et al. 1984 "Histo-pathological Studies of Synthetic Hydroxyapatite Applied as Root Canal Filling Materials to Apical Wounds of Dog Teeth (Part 1)" *The Japanese Journal of conservative Dentistry* 27: 190-199.
Nakao and Tsuji, "Dental regenerative therapy: Stem cell transplantation and bioengineered tooth replacement", (2008), Japanese Dental Science Review, 44, 70-75.
Nakashima, M. and Akamine, A. 2005 "The Application of Tissue Engineering to Regeneration of Pulp and Dentin in Endodontics" *Journal of Endodontics* 31: 711-718.
Nakashima, M. and Reddi, A.H. 2003 "The application of bone morphogenetic proteins to dental tissue engineering" *Nature Biotechnology* 21: 1025-1032.
Nakashima, et al., 2006; Gene Therapy for Dentin Regeneration with Bone Morphogenetic Proteins, Current Gene Therapy, 6, No. 5, pp. 551-560.
Nakashima, M. 2007 "Tissue engineering of teeth" *Handbook of Biomineralization* 3 *(Medical and Clinical Aspects)*: 265-281.
Nakashima, M, et al, 2009: "Human dental pulp stems with highly angiogenic and neurogenic potential for possible use in pulp regenartion", *Cytokine & Growth Factor Reviews*, 20(6): 435-440.
Sloan, et al., 2007: "Stem cells and the dental pulp: potential roles in dentine regeneration and repair", Oral Diseases, 13, No. 2, pp. 151-157.
Soukup, T, et al, 2006: "Biological properties and flow cytometric analysis of human dental pulp stem cells", *Cytotherapy, Isis Medical Media*, 8(2): 3.
Tsutsui, T. et al., "Acceleration of calcification by co-culture of epithelial cells derived from human gum and fibroblasts, and epithelial cells derived from human gum and dental pulp cells" Journal of Oral Biosciences vol. 47, Suppl. 2005, p. 155, 324 2P.

(56) References Cited

OTHER PUBLICATIONS

Tsutsui, T. et al., "Calcification under co-culture of pithelial cells and mesenchymal cells" Oral Tissue Culture Association Magazine, vol. 16 (1), 2007 pp. 11-12.

Yang et al. "The Design of Scaffolds for Use in Tissue Engineering. Part I, Traditional Factors." 2001, Tissue Engineering, 7(6), 679-689.

Yoshiyama, M., et al., "Seeking a New Caries Treatment: New Conversion from Restoration to Dentin Regeneration" Japan Association for Dental Science Magazine, vol. 22, 2003, pp. 76-80.

Zhang, W. et al. 2006 "The performance of human dental pulp stem cells on different three-dimensional scaffold materials" *Biomaterials* 27: 5658-5668.

Otsuri, S. et al., 2007 "Mechanism of involvement of bone marrow precursor cells in organism bone formation process" *J Jpn Orthop Assoc* 81(8): 1-5-PD3-1.

Yoshida, M. et al., 2005 "Bone marrow stem cells as tools for cell transplantation" *Pharma Medica* 23(10): 59-64.

Hasegawa, et al. 2008 "Effects of G-CSF on vascularization and chronic ischemic heart disease" *Total Clinical* 57(2): 236-241.

* cited by examiner

Pulp CD105+
(+) (-)

Neurofilament

Neuromodulin

Scn1a

β-actin

FIG.10M
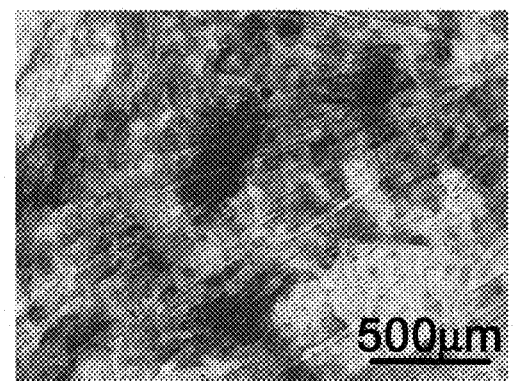
FIG.10N
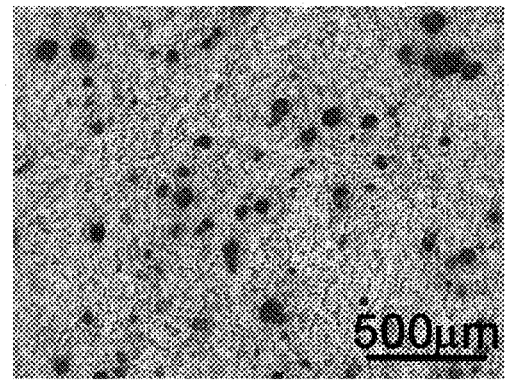
FIG.10O

UNEXTRACTED TOOTH ROOT CANAL FILLER AND DENTAL TISSUE REGENERATION METHOD FOR UNEXTRACTED TOOTH

TECHNICAL FIELD

The present disclosure relates to unextracted tooth root canal fillers for filling root canals of unextracted teeth, and dental tissue regeneration methods for unextracted teeth using the unextracted tooth root canal fillers.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 16823710_1.TXT, the date of creation of the ASCII text file is Dec. 10, 2013, and the size of the ASCII text file is 11.4 KB.

BACKGROUND ART

At present, about a half of tooth loss is due to dental caries and tooth fractures, and it is known that removal of dental pulp greatly increases the possibility of tooth loss.

The average lifetime of teeth is said to be 57 years at present. To enable a person to chew with his/her own teeth throughout the lifetime, the lifetime of teeth needs to be prolonged by 20 years or more. Despite of "8020" Campaign (to keep 20 teeth or more until 80 years old), people now aged 80 keep about 8 teeth on average, and the number of remaining teeth of elderly people has hardly increased. Thus, dental caries treatment requires drastic improvement.

When dental pulp is removed (pulpectomy), its potential of reparative dentin formation and defense mechanism against infection are lost, and an alarm signal, i.e., a pain, is lost, thereby increasing the danger of enlarged dental caries. In addition, there are no perfect methods for the pulpectomy treatment, and leakage from a tooth crown part after pulpectomy and root canal filling might cause a periapical lesion, a vertical fracture, an aesthetic loss, and a postoperative pain.

In view of this background, it is very important in this unprecedented aging society not to casually perform pulpectomy but to develop a new treatment for dental caries and pulpitis by regeneration of dentin and dental pulp incorporating dental regenerative medicine technology in order to prolong the lifetime of teeth.

Regarding dentin regeneration, as cell therapy or gene therapy, proteins such as bone morphogenetic proteins (BMP) or genes are introduced into dental pulp stem cells/progenitor cells in vitro, to stimulate differentiation into odontoblasts in three-dimensional culture, and the odontoblasts are autologously transplanted on an amputated vital pulp together with its extracellular matrix. Thereby, a large amount of dentin is formed (see NON-PATENT DOCUMENTS 1 and 2).

However, in a case of pulpitis, it is necessary to regenerate dental pulp tissue as well as dentin.

The dental pulp tissues are very rich in blood vessels and nerves. The dental pulp has potential to heal spontaneously. Specifically, when being injured, chemotactic factors are locally released, and stem cells migrate from the periphery of blood vessels in the deeper part of the dental pulp to the injured site, proliferate and differentiate, leading to angiogenesis and reparative dentin formation. In particular, the vasculature of dental pulp is important for supplying nutrition and oxygen, serving as a conduit for metabolite waste, and homeostasis in the dental pulp. The dental pulp innervation plays an important role in adjusting a blood flow, a liquid flow into dentinal tubules, and the internal pressure of the dental pulp, regulating inflammation, being involved in angiogenesis and infiltration of immunocompetent cells or inflammatory cells, and contributes to homeostasis in the dental pulp and reinforcement of defense reaction of the dental pulp. Accordingly, in dentin/dental pulp regeneration, interaction between blood vessels and nerves, angiogenesis, and nerve regeneration need to be taken into consideration.

SP cells include $CD31^-/CD146^-SP$ cells and $CD31^-/CD146^+SP$ cells in a ratio of about 1:1. As compared to the $CD31^-/CD146^+SP$ cells, the $CD31^-/CD146^-SP$ cells significantly promote angiogenesis, nerve regeneration, and dental pulp regeneration, and significantly express CXCR4 mRNA, a chemokine receptor to stromal cell-derived factor-1 (SDF-1).

It is known that SDF-1 is secreted from a wounded portion of, for example, the skin, migration of human stem cells to SDF-1 depends on expression of CXCR4. The CXCR4 is also called a marker of stem cells, and embryonic stem cell-like cells are fractionated as $CXCR4^+/SSEA-4^+/Oct-4^+$ from human cord blood (see NON-PATENT DOCUMENT 3).

As nerve stem cells, $CXCR4^+/SSEA-1^+$ cells which migrate to central nerves and have remarkable potential for nerve differentiation, are fractionated from a mouse fetal brain (see NON-PATENT DOCUMENT 4).

It is said that CXCR4-positive cells are pluripotent cells and CXCR4 can be used to fractionate stem and progenitor cells which have potential for differentiation into cells secreting insulin in human pancreata (see NON-PATENT DOCUMENT 5).

On the other hand, regarding dental pulp regeneration, it has been said to date that dental pulp in a tooth with incomplete apical closure is regenerated after extraction followed by root canal treatment and replantation. It is reported that even in the case of a tooth with an incomplete root having a periapical lesion, dental pulp-like tissues are regenerated in the following manner. After extraction of a tooth, the root canal is thoroughly enlarged and cleaned, and filled with blood clot to the cementodentinal junction so that the cavity is completely sealed with mineral trioxide aggregate (MTA).

It is also reported that dental pulp-like tissues in a canine healthy tooth with a complete apical closure are regenerated by pulpectomy after tooth extraction, cutting of the apical part or enlarging the apical area to 1.1 mm or more, followed by replantation and filling the root canal with blood clot (see NON-PATENT DOCUMENT 6).

Most of the above reports on the dental pulp regeneration in the root canal are directed to immature teeth with incomplete roots, and it has not been proved yet that regenerated tissues in the root canal are specific to dental pulp including blood vessels and nerves. In addition, in all the reports, enlargement and cleaning of the root canal are performed in vitro after temporary extraction of a tooth, and the root canal is then filled with blood clot after replantation of the tooth.

CITATION LIST

Non-Patent Document

[NON-PATENT DOCUMENT 1] Nakashima and Reddi, 2003 (PMID: 12949568 doi 10.1038/nbt864)

[NON-PATENT DOCUMENT 2] Nakashima and Akamine, 2006 (PMID: 16186748)

[NON-PATENT DOCUMENT 3] Kucia M et al., 2007 (PMID: 17136117doi: 10.1038/sj.leu.2404470)

[NON-PATENT DOCUMENT 4] Corti S et al., 2005 (PMID: 16150803 doi: 10.2478/v10042-008-0045-0)

[NON-PATENT DOCUMENT 5] Koblas T et al., 2007 (PMID: 17328838)

[NON-PATENT DOCUMENT 6] Laureyset et al., 2001 (PMID: 11298308doi: 10.1067/mod.2001.113259)

SUMMARY OF THE INVENTION

Technical Problem

In some cases, however, idiopathic resorption (internal resorption) of the tooth substance occurs in dentin of the pulp cavity or the root canal after extraction, followed by enlargement and disinfection of a root canal in vitro and replantation of the tooth and filling of the root canal with blood clot. If this internal resorption grows, perforation might occur in the dentin. In case of a general clinical technique of transplantation of a normal wisdom tooth with a complete root into another missing part of tooth, dental agitation or loss of the tooth due to internal or external resorption might arise several years after transplantation. In addition, for a tooth with a complete apical closure, a dental pulp tissue regeneration method in pulpectomy or infected root canal treatment has not been established yet, and a root canal filler for dental pulp tissue regeneration has not been established, either.

It is therefore an object of the present disclosure to provide a new original root canal filler for dental tissue regeneration which causes neither internal resorption nor and external resorption and no odontoclasts and exhibits alignment of odontoblasts along the dentinal wall, and also provide a dental tissue regeneration method using such a root canal filler.

Solution to the Problem

An unextracted tooth root canal filler in a first aspect of the present disclosure is formed to be inserted in an apical part of the root canal after pulpectomy, or enlargement and disinfection of the infected root canal without tooth extraction, and the unextracted tooth root canal filler includes: dental pulp stem cells and an extracellular matrix.

The dental pulp stem cells preferably include at least one of dental pulp CXCR4-positive cells, SSEA-4-positive cells, FLK-1-positive cells, CD105-positive cells, dental pulp SP cells, CD31-negative and CD146-negative cells, CD24-positive cells, CD150-positive cells, CD29-positive cells, CD34-positive cells, CD44-positive cells, CD73-positive cells, or CD90-positive cells.

The dental pulp SP cells are preferably CXCR4-positive cells, SSEA-4-positive cells, FLK-1-positive cells, CD31-negative and CD146-negative cells, CD24-positive cells, CD105-positive cells, CD150-positive cells, CD29-positive cells, CD34-positive cells, CD44-positive cells, CD73-positive cells, or CD90-positive cells.

Preferably, in the unextracted tooth root canal filler, the dental pulp stem cells are localized to the apical part of the root canal, and a chemotactic factor including at least one of a cell chemotactic factor, a cell growth factor, a neurotrophic factor, or an angiogenic factor is localized to a tooth crown part of the root canal.

The cell chemotactic factor is preferably at least one of SDF-1, VEGF, G-CSF, SCF, MMP3, Slit, or GM-CSF.

The cell growth factor is preferably at least one of IGF, bFGF, or PDGF.

The neurotrophic factor is preferably at least one of GDNF, BDNF, NGF, Neuropeptide Y, or Neurotrophin 3.

The extracellular matrix is preferably made of biocompatible material containing at least one of collagen, synthetic proteoglycans, gelatin, hydrogel, fibrin, phosphophorin, heparan sulfate, heparin, laminin, fibronectin, alginic acid, hyaluronic acid, chitin, PLA, PLGA, PEG, PGA, PDLLA, PCL, hydroxyapatite, β-TCP, calcium carbonate, titanium, or gold.

A concentration of the dental pulp stem cells in the extracellular matrix is preferably in the range from $1 \times 10^3$ cells/μl to $1 \times 10^6$ cells/μl, both inclusive.

A dental tissue regeneration method without extraction in a second aspect of the present disclosure, dental tissues in a root canal are regenerated by injecting an unextracted tooth root canal filler including dental pulp stem cells and an extracellular matrix into an apical part of the root canal after pulpectomy, or enlargement and disinfection of the infected root canal without tooth extraction.

The dental pulp stem cells preferably include at least one of dental pulp CXCR4-positive cells, SSEA-4-positive cells, FLK-1-positive cells, CD105-positive cells, dental pulp SP cells, CD31-negative and CD146-negative cells, CD24-positive cells, CD150-positive cells, CD29-positive cells, CD34-positive cells, CD44-positive cells, CD73-positive cells, or CD90-positive cells.

The dental pulp SP cells are preferably CXCR4-positive cells, SSEA-4-positive cells, FLK-1-positive cells, CD31-negative and CD146-negative cells, CD24-positive cells, CD105-positive cells, CD150-positive cells, CD29-positive cells, CD34-positive cells, CD44-positive cells, CD73-positive cells, or CD90-positive cells.

Preferably, in the unextracted tooth root canal filler, the dental pulp stem cells are localized to the apical part of the root canal, and a chemotactic factor including at least one of a cell chemotactic factor, a cell growth factor, a neurotrophic factor, or an angiogenic factor is transplanted to a tooth crown part of the root canal.

The cell chemotactic factor is preferably at least one of SDF-1, VEGF, G-CSF, SCF, MMP3, Slit, or GM-CSF.

The cell growth factor is preferably at least one of IGF, bFGF, or PDGF.

The neurotrophic factor is preferably at least one of GDNF, BDNF, NGF, Neuropeptide Y, or Neurotrophin 3.

The extracellular matrix is preferably made of a biocompatible material containing at least one of collagen, synthetic proteoglycans, gelatin, hydrogel, fibrin, phosphophorin, heparan sulfate, heparin, laminin, fibronectin, alginic acid, hyaluronic acid, chitin, PLA, PLGA, PEG, PGA, PDLLA, PCL, hydroxyapatite, β-TCP, calcium carbonate, titanium, or gold.

The root canal is preferably enlarged before injection of the root canal filler into the apical part of the root canal, thereby enlarging the root canal in an apical area to a predetermined size.

A concentration of the dental pulp stem cells in the extracellular matrix is preferably in the range from $1 \times 10^3$ cells/μl to $1 \times 10^6$ cells/μl, both inclusive.

Advantages of the Invention

According to the present disclosure, dental tissues can be regenerated in a tooth with a complete apical closure, causing neither internal resorption nor external resorption and no odontoclasts, and exhibiting alignment of odontoblasts along the dentinal wall.

BRIEF DESCRIPTION OF THE DRAWINGS

FIG. 10M is a photograph showing the dentinogenic/osteogenic induction of unfractionated total dental pulp cells on the 28th day.

FIG. 10N is a photograph showing the dentinogenic/osteogenic induction of adipose CD105-positive cells on the 28th day.

FIG. 10O shows a comparison of potential of odontoblastic differentiation among dental pulp CD105-positive cells, unfractionated total dental pulp cells, and adipose CD105-positive cells.

DESCRIPTION OF EMBODIMENTS

First Embodiment

Embodiments of the present disclosure will be specifically described hereinafter with reference to the drawings. An unextracted tooth root canal filler according to this embodiment includes dental pulp stem cells and an extracellular matrix, and is inserted in the apical part of an infected root canal of an unextracted tooth after pulpectomy or enlargement and cleaning of the root canal.

Figure 1:
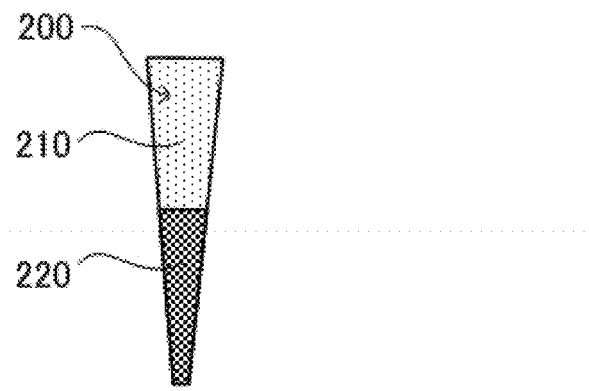
FIG. 1 is a view for illustrating an unextracted tooth root canal filler according to a first embodiment.

FIG. 1 is a view illustrating an unextracted tooth root canal filler 200 according to this embodiment. The unextracted tooth root canal filler 200 is formed by transplanting dental pulp stem cells 220 to an extracellular matrix 210. The dental pulp stem cells 220 are transplanted to the apical part of the root canal of the unextracted tooth root canal filler 200.

The dental pulp stem cells are dental pulp stem cells derived from a permanent tooth or a deciduous tooth. The dental pulp stem cells include at least one of dental pulp CXCR4-positive cells, SSEA-4-positive cells, FLK-1-positive cells, CD105-positive cells, dental pulp SP cells, CD31-negative and CD146-negative cells, CD24-positive cells, CD150-positive cells, CD29-positive cells, CD34-positive cells, CD44-positive cells, CD73-positive cells, or CD90-positive cells. For example, canine permanent tooth dental pulp cells include 0.8% CXCR4-positive cells and have a high tissue regeneration potential such as an angiogenic potential.

The dental pulp SP cells are preferably CXCR4-positive cells, SSEA-4-positive cells, FLK-1-positive cells, CD31-negative and CD146-negative cells, CD24-positive cells, CD105-positive cells, CD150-positive cells, CD29-positive cells, CD34-positive cells, CD44-positive cells, CD73-positive cells, or CD90-positive cells.

When CD31$^-$/CD146$^-$ side population (SP) cells are transplanted in a mouse hindlimb ischemic site, blood flow recovery and angiogenesis are promoted. When these SP cells are transplanted in a cerebral infarction ischemic site of a rat, nerve cell differentiation is promoted and motor disability is recovered. In addition, when these SP cells are transplanted in a canine amputated pulp, angiogenesis, nerve regeneration, and dental pulp regeneration are observed in a cavity on the amputated vital pulp. In this manner, in the case of using CD31$^-$/CD146$^-$SP cells as dental pulp stem cells, potential of dental pulp regeneration is assumed to be high. However, to fractionate SP cells, cells need to be labeled with Hoechst 33342, which is a DNA-binding fluorescent dye, and thus, safety problems might occur in clinical application.

On the other hand, dental pulp CXCR4-positive cells can be fractionated by a migration method using SDF-1, AMD3100, or G-CSF, for example, without using flow cytometry, which cannot be clinically employed because of the possibility of contamination, and an antibody bead technique, which is expensive and thus has a limited use. For this reason, the dental pulp CXCR4-positive cells can be fractionated with safety at low cost. Accordingly, in the case of using CXCR4-positive cells as dental pulp stem cells, the CXCR4-positive cells can be clinically used promptly, and are economically advantageous.

The dental pulp stem cells may be autologous cells extracted from a target animal itself to be subjected to treatment for dental tissue regeneration, or may be allogeneic cells extracted from an another distinct animal from the target animal to be subjected to treatment for dental tissue regeneration.

The concentration of dental pulp stem cells in the unextracted tooth root canal filler 200 is preferably in the range from $1 \times 10^3$ cells/μl to $1 \times 10^6$ cells/μl, both inclusive. This is because of the following reasons. If the concentration of dental pulp stem cells is less than $1 \times 10^3$ cells/μl, dental tissues in a root canal are insufficiently regenerated. On the other hand, if the cell concentration of dental pulp stem cells is larger than $1 \times 10^6$ cells/μl, an unexpected adverse reaction might occur in the target tooth.

The extracellular matrix (Scaffold) 210 is preferably made of a biocompatible material containing at least one of collagen, synthetic proteoglycans, gelatin, hydrogel, fibrin, phosphophorin, heparan sulfate, heparin, laminin, fibronectin, alginic acid, hyaluronic acid, chitin, polylactic acid (PLA), lactic acid/glycolic acid copolymers (PLGA), polyethylene glycol (PEG), polyglycol acid (PGA), poly-DL-lactic acid (PDLLA), polycaprolactone (PCL), hydroxyapatite, β-TCP, calcium carbonate, titanium, or gold. The proteoglycans above are composite sugars consisting of proteins and sugar chains (glucosaminoglycans) covalently bound to each other. The extracellular matrix may be a sponge-shaped three-dimensional structure made of nanofibers each having a number-average diameter of 1 nm to 1000 nm and prepared with a polymer such as thermoplastic polymer. The void rate of such a three-dimensional structure is preferably 80% to 99.99%.

Collagen to be used as the extracellular matrix is preferably a mixture of type I collagen and type III collagen. The type I collagen is basic collagen, which is fibrous. The type III collagen forms a fine network structure, called reticular fiber different from the collagen fiber, and provides a matrix for fixation of cells and others.

The proportion of the type III collagen in the collagen mixture described above is preferably in the range from 30 weight % (wt. %) to 50 wt. %, both inclusive. This is because of the following reasons. If the proportion of the type III collagen is higher than 50 wt. %, the collagen mixture might not be solidified. On the other hand, if the proportion of the type III collagen is lower than 10 wt. %, the proportion of the type I collagen increases, and not angiogenesis described below but regeneration of dentin might occur.

Figure 2:
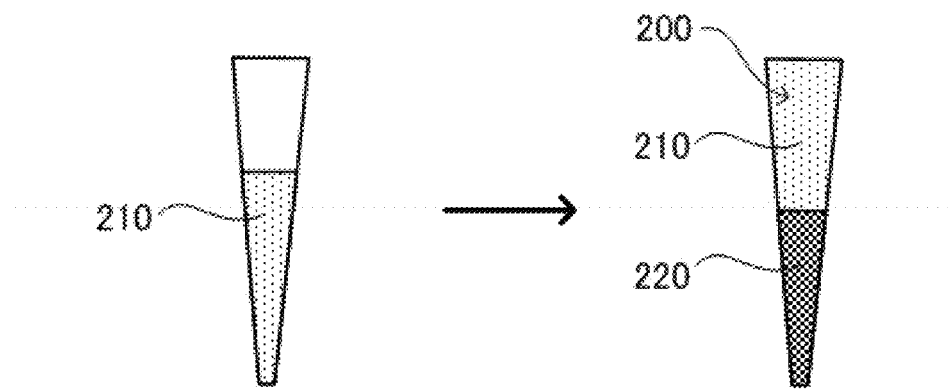
FIG. 2 is a view showing a process for forming the unextracted tooth root canal filler of the first embodiment.

Referring now to FIG. 2, a method for forming an unextracted tooth root canal filler 200 according to this embodiment will be described. FIG. 2 is a view showing a method for forming an unextracted tooth root canal filler 200.

An unextracted tooth root canal filler 200 is formed by transplanting dental pulp stem cells 220 to the apical part of an extracellular matrix 210. The dental pulp stem cells 220 are preferably transplanted to ¼ to ⅔ of the apical part of the unextracted tooth root canal filler 200, and more preferably transplanted to ⅓ of the apical part. In an example of the method for forming a root canal filler, 10 µl to 13 µl of the type I and III collagen mixture is first absorbed, and 7 µl to 10 µl of the type I and III collagen mixture (e.g., collagen XYZ, Nitta Gelatin) including dental pulp stem cells is then absorbed, into the tip of Pipetman, for example, to a total amount of 20 µl. Absorption into the tip of Pipetman, for example, is preferably slow enough to prevent formation of air bubbles. This is because if air bubbles are formed in the root canal filler, the bubbles restrain migration of cells to inhibit acceleration of dental tissue regeneration. The internal diameter of the Pipetman tip is preferably small and may be 0.5 to 0.7 mm at the bottom of the tip, for example. For example, H-010-96RS microcapillary tip from QSP may be used. The shape of the unextracted tooth root canal filler is not specifically limited, and may be a cone, a truncated cone, or a cylinder, for example.

Referring now to FIGS. 3A-3F, a dental tissue regeneration method using the unextracted tooth root canal filler 200 will be described.

Figure 3A:
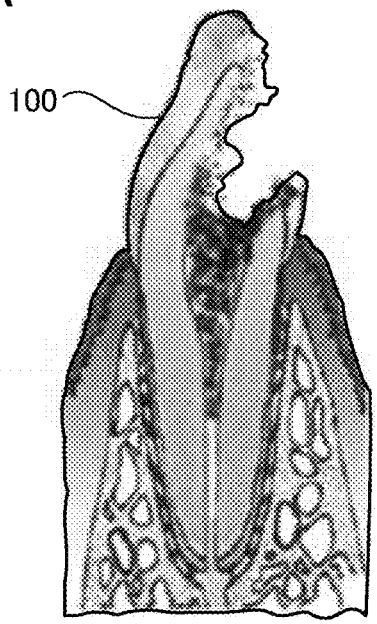
FIG. 3A is a view for explaining a tooth with pulpitis.

As shown in FIG. 3A, in the dental pulp tissue regeneration method of this embodiment, dental tissue regeneration is performed on an unextracted target tooth 100 with, for example, pulpitis. The target tooth 100 is a tooth in which microbial infection reaches the coronal pulp or the radicular pulp because of caries or pulpitis, for example.

Figure 3B:
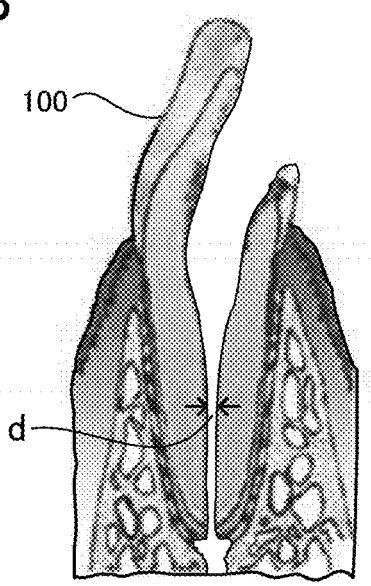
FIG. 3B is a view schematically showing root canal enlargement after pulpectomy.

As shown in FIG. 3B, the target tooth 100 is subjected to pulpectomy or enlargement and cleaning of the infected root canal. Pulpectomy is an operation to remove the dental pulp present in the tooth. The infected root canal is a root canal in which microbes reach the dental pulp and additionally to dentin of the root canal wall. The phrase "after enlargement and cleaning of the root canal" means after removal of the microbes in the infected root canal.

After pulpectomy, it is preferable to adjust the size of the apical foramen to a predetermined width by enlargement of the root canal of the target tooth. As will be described below, this is because of the following reasons. In filling the root canal subjected to pulpectomy or treatment for the infected root canal with the unextracted tooth root canal filler 200, enlargement of the root canal can ease the filling with the unextracted tooth root canal filler 200, and allows blood vessels and nerves to easily penetrate therein from apical periodontal tissues. The apical area herein is a terminal of a target tooth (i.e., the apex area of the root of the tooth) connected to the alveolar bone.

For example, in FIG. 3B, the width d of the apical foramen, i.e., the diameter of root canal, is preferably in the range from 0.7 mm to 1.5 mm, both inclusive. This is because of the following reasons. If the width d of the apical foramen is less than 0.7 mm, blood vessels and nerves do not easily penetrate therein from apical periodontal tissues, and it might be difficult to fill the canal with the unextracted tooth root canal filler 200. On the other hand, if the width d of the apical foramen is more than 1.5 mm, enlargement of the root canal may lead to application of a load more than needed on the target tooth, thus causing a tooth fracture.

Figure 3C:
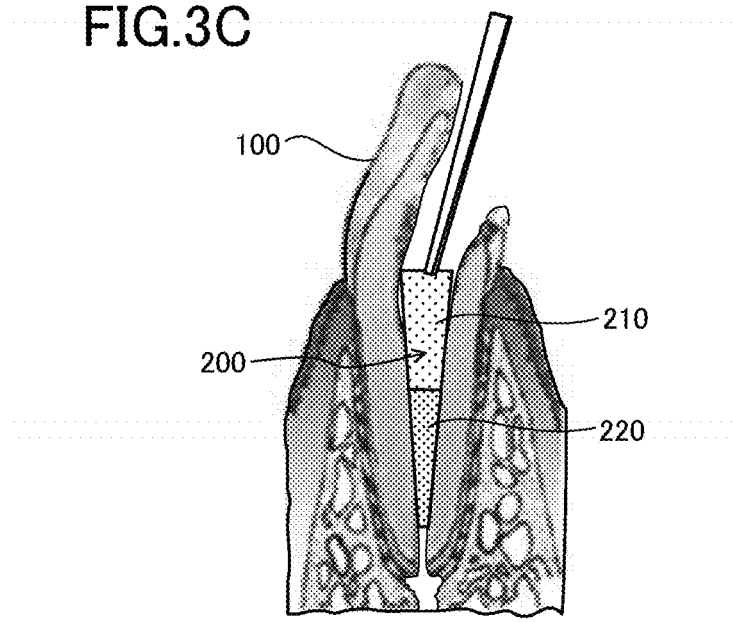
FIG. 3C is a view schematically showing filling with an unextracted tooth root canal filler.

Then, as shown in FIG. 3C, the unextracted tooth root canal filler 200 is inserted into the apical part of the root canal with, for example, tweezers. Since the unextracted tooth root canal filler 200 contains biological materials, the unextracted tooth root canal filler 200 may be a biological root canal filler. The unextracted tooth root canal filler 200 is preferably inserted into a site corresponding to a region where the dental pulp in the root canal existed. In a case where the extracellular matrix 210 is gel, the extracellular matrix 210 cannot be held with tweezers, and thus, is injected with Pipetman or a syringe, for example.

Figure 3D:
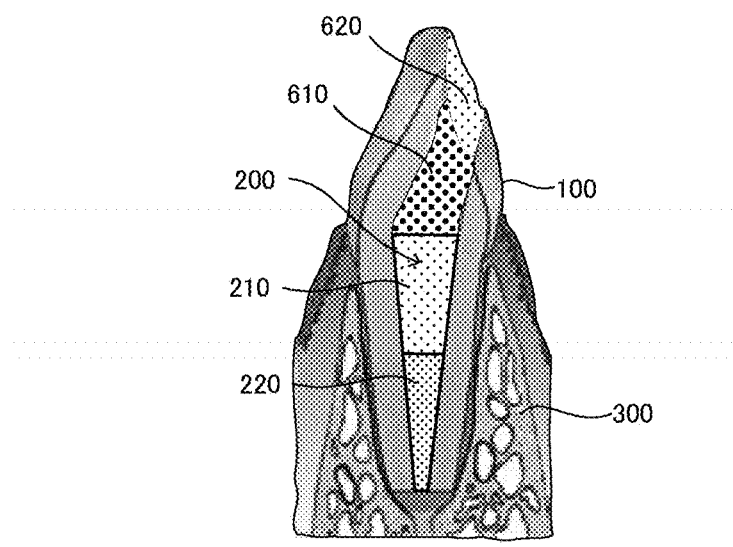
FIG. 3D is a view schematically showing injection of Spongel (gelatin) and resin.

After injection of the unextracted tooth root canal filler 200 into the apical part of the root canal, as shown in FIG. 3D, gelatin 610 is injected into a region above unextracted tooth root canal filler 200 and the root canal is capped with a resin 620.

Figure 3E:
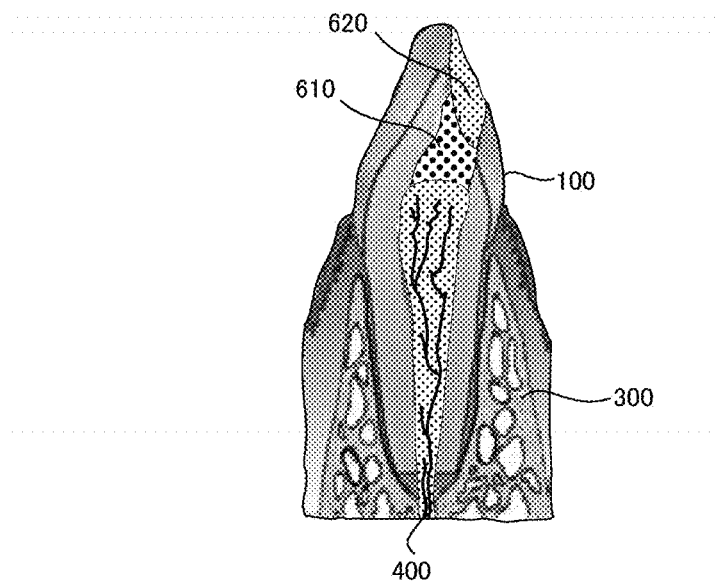
FIG. 3E is a view schematically showing dental pulp regeneration and angiogenesis.

In this manner, dental tissues in the root canal are regenerated. As shown in FIG. 3E, dental tissues to be regenerated are, for example, tissues specific to dental pulp in the root canal, blood vessels 400, or nerves. Examples of dental tissues to be regenerated by using morphogen such as BMPs include dentin. In addition, in the case of filling an infected root canal with the unextracted tooth root canal filler 200, examples of dental tissues to be regenerated include periodontal tissues such as periodontiums (i.e., periodontal tissues for planting a tooth on an alveolar bone) and cementum.

Figure 3F:
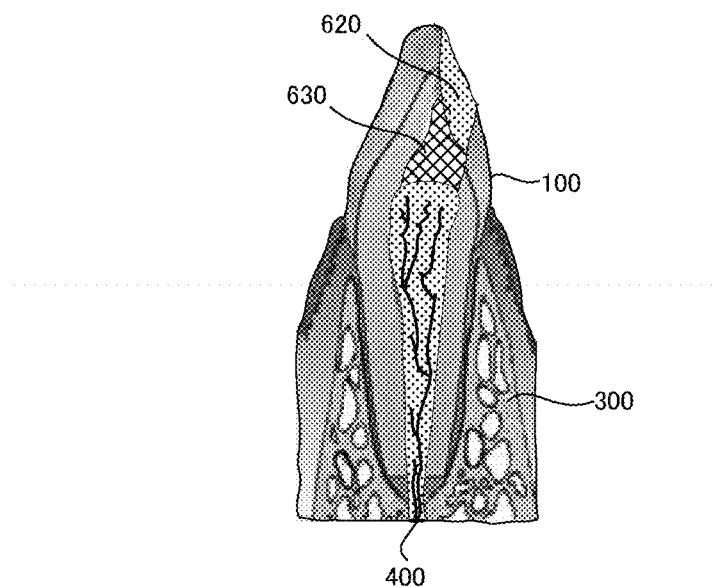
FIG. 3F is a view schematically showing injection of a morphogen and resin.
Figure 3G:
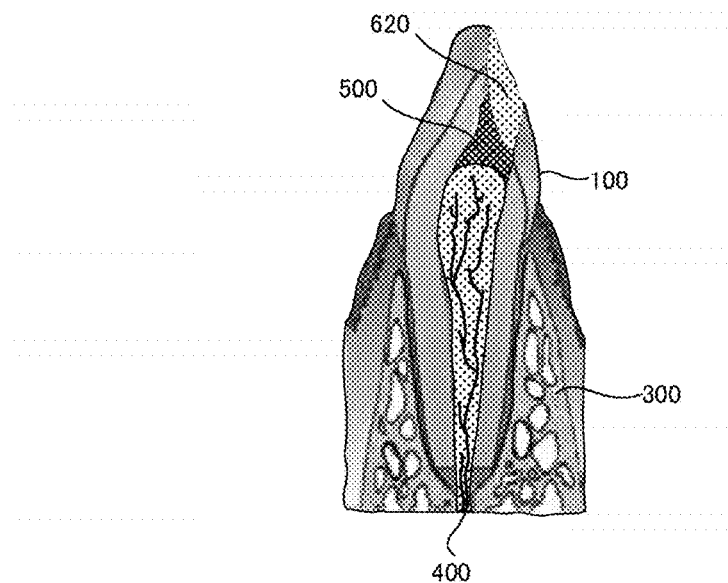
FIG. 3G is a view schematically showing dentin regeneration.
Figure 3H:
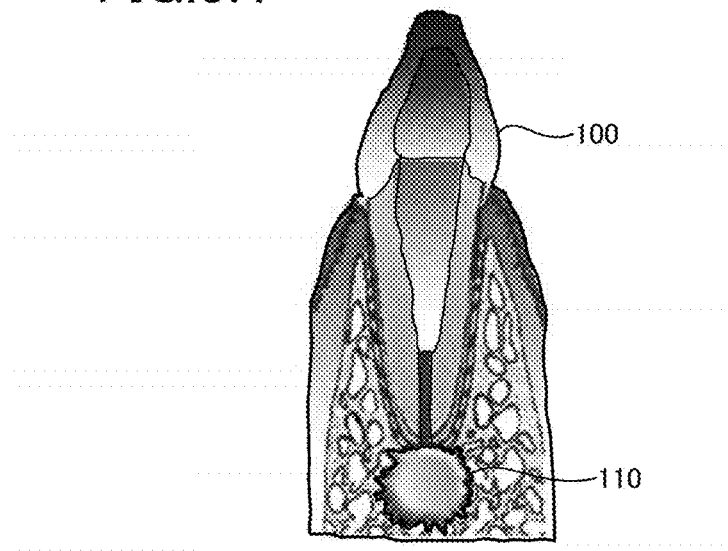
FIG. 3H is a view schematically showing periapical periodontitis in which microbes reach the dental pulp and further reach dentin in the root canal wall and apical periodontal tissues.

Subsequently, the resin 620 is temporarily removed, and as shown in FIG. 3F, a morphogen 630 such as BMP or a growth/differentiation factor is applied on the tooth-crown dental pulp, and the root canal is capped with the resin 620. The application of the morphogen 630 or the growth/differentiation factor on the tooth-crown dental pulp allows dentin 500 to be also regenerated, as shown in FIG. 3G.

In the dental tissue regeneration using the unextracted tooth root canal filler 200 of this embodiment, none of internal resorption and external resorption is observed in the regenerated tissues, no odontoclast is observed either, and odontoblasts are aligned along the dentinal wall. Although a large amount of blood clots generated by bleeding is expected to be an obstacle of regeneration of dental pulp tissues, the use of an unextracted tooth in this embodiment can reduce generation of blood clots, thereby efficiently promoting regeneration of dental tissues. In addition, since an unextracted tooth is used in this embodiment, filling of a root canal can be delayed with medication of the root canal until bleeding or symptoms after enlargement of the root canal disappears. Thus, the method of this embodiment can approach an actual clinical treatment.

In the above description, the target tooth 100 is a tooth in which microbial infection reaches the coronal pulp or the radicular pulp because of caries or pulpitis, for example. However, the present disclosure is not limited to this tooth, and the target tooth 100 includes a tooth having a degraded nerve function to have a weak sense of occlusion. In such a case, the unextracted tooth root canal filler 200 is injected after pulpectomy to regenerate dental pulp. Then, the sense of occlusion can be improved. In addition, the target tooth 100 also includes a tooth in which microbial infection reaches apical periodontal tissues (i.e., a tooth in which microbes reaches the dental pulp and further reaches dentin in the root canal wall and apical periodontal tissues). Such a tooth often involves periapical periodontitis 110. After enlargement and cleaning of the infected root canal, the unextracted tooth root canal filler 200 is injected.

Second Embodiment

Figure 4A:
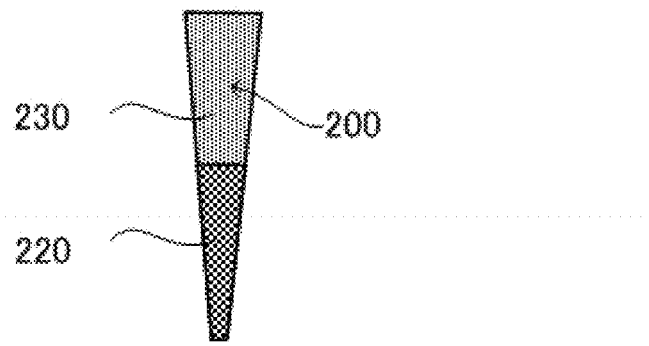
FIG. 4A is a view illustrating an unextracted tooth root canal filler in which a chemotactic factor is transplanted to the tooth crown part of a root canal.
Figure 4B:
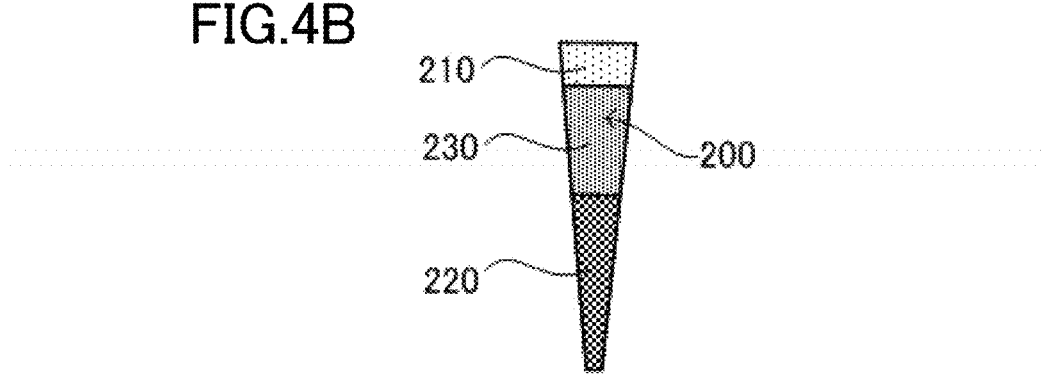
FIG. 4B is a view illustrating an unextracted tooth root canal filler in which a chemotactic factor is transplanted to the tooth crown part of a root canal and an extracellular matrix remains at the tooth crown part.

FIGS. 4A and 4B are views illustrating an unextracted tooth root canal filler 200 according to a second embodiment of the present disclosure. As illustrated in FIG. 4A, in the unextracted tooth root canal filler 200, dental pulp stem cells 220 are transplanted to the apical part of the root canal, and a chemotactic factor 230 containing at least one of a cell chemotactic factor, a cell growth factor, a neurotrophic factor, or an angiogenic factor is transplanted to the tooth crown part of the root canal (e.g., ½ to ⅔ from the upper end of the root canal).

The reason why the dental pulp stem cells 220 are transplanted to the apical part of the root canal and the chemotactic factor 230 is transplanted to the tooth crown part of the root canal is as follows. Even after the dental pulp stem cells 220 are transplanted to the tooth crown part of the root canal, failures in supplying nutrition from tissues might occur to cause a necrosis. In addition, the dental pulp stem cells 220 transplanted to the apical part of the root canal are likely to be pulled by the chemotactic factor transplanted to the tooth crown part of the root canal to promote regeneration of dental tissues. Alternatively, as illustrated in FIG. 4B, an extracellular matrix 210 may remain in the unextracted tooth root canal filler 200 at the tooth crown part of the root canal.

The cell chemotactic factor means a molecule which activates a signal transduction involved in cell migration when the molecule binds to the receptor. The cell growth factor means a molecule which activates a signal transduction involved in cell growth when the molecule binds to the receptor. The neurotrophic factor means a molecule which activates a signal transduction involved in cell survival when the molecule binds to the receptor. The angiogenic factor means a molecule which activates a signal transduction involved in growth, migration, and anti-apoptosis of vascular endothelial cells when the molecule binds to the receptor.

The cell chemotactic factor is preferably at least one of SDF-1, VEGF, G-CSF, SCF, MMP3, Slit, or GM-CSF. In particular, MMP3 has a high cell migration potential, and thus is preferably used.

The cell growth factor is preferably at least one of IGF, bFGF, or PDGF.

The neurotrophic factor is preferably at least one of GDNF, BDNF, NGF, Neuropeptide Y, or Neurotrophin 3.

The angiogenic factor is preferably at least one of E-selectin, VCAM1, ECSCR, or SLC6A6.

The concentration of the chemotactic factor in the extracellular matrix to which the chemotactic factor is transplanted is preferably in the range from 0.1 ng/µl to 500 ng/µl, both inclusive. This is because of the following reasons. If the concentration of the chemotactic factor is lower than 0.1 ng/µl, migration might be less stimulated. On the other hand, if the concentration of the chemotactic factor is higher than 500 ng/µl, an unexpected adverse reaction might occur in the target tooth 100.

Figure 5:
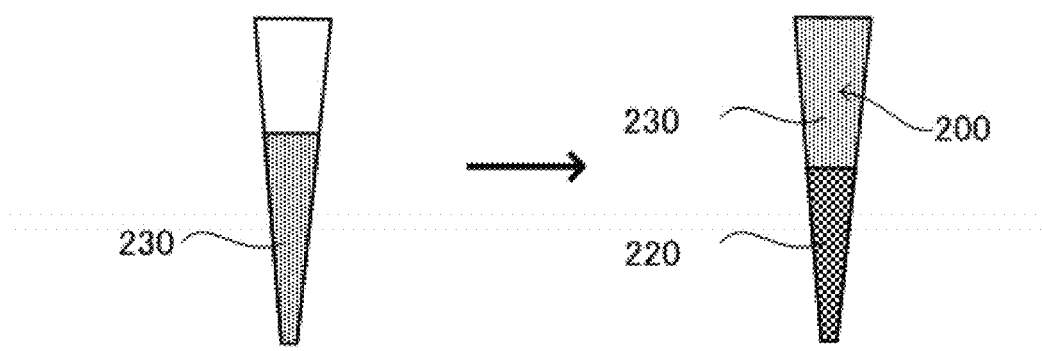
FIG. 5 shows a process of forming an unextracted tooth root canal filler according to a second embodiment.

Referring now to FIG. 5, a method of formation of an unextracted tooth root canal filler 200 according to this embodiment will be described. FIG. 5 shows a method of formation of an unextracted tooth root canal filler 200 in which a chemotactic factor 230 is transplanted to the tooth crown part of a root canal.

In an example method of formation of an unextracted tooth root canal filler 200 according to the second embodiment, 10 µl to 13 µl of a type I and III collagen mixture (where the mixture ratio between type I collagen and type III collagen is 1:1) including a chemotactic factor is first absorbed, and 7 µl to 10 µl of a type I and III collagen mixture including dental pulp stem cells is then absorbed, into the tip of Pipetman, for example, to a total amount of 20 µl. In the second embodiment, absorption into the tip of Pipetman, for example, is also preferably slow enough to prevent formation of air bubbles. The internal diameter of the tip of Pipetman is preferably small. In this manner, a root canal filler 200 illustrated in FIG. 4A can be obtained.

In the same manner as in the first embodiment, the unextracted tooth root canal filler 200 of the second embodiment is injected into the apical part of the root canal without tooth extraction after pulpectomy or after enlargement and cleaning of the infected root canal.

The unextracted tooth root canal filler 200 of this embodiment includes the chemotactic factor. Accordingly, dental tissues can be more efficiently regenerated without internal resorption and odontoclast differentiation in the regenerated tissues, and odontoblasts are aligned along the dentinal wall.

Third Embodiment

In the unextracted tooth root canal filler 200 of the first embodiment, the dental pulp stem cells 220 are transplanted to the apical part of the root canal. However, the present disclosure is not limited to this example, and the dental pulp stem cells 220 may be uniformly mixed in the entire unextracted tooth root canal filler 200. In such an unextracted tooth root canal filler 200, dental tissues can be regenerated in a tooth with a complete apical closure, without internal resorption, external resorption and odontoclast differentiation in the regenerated tissues, and odontoblasts are aligned along the dentinal wall.

This unextracted tooth root canal filler 200 can be obtained by, for example, uniformly mixing dental pulp stem cells with a type I and III collagen mixture (e.g., collagen XYZ, Nitta Gelatin) without formation of bubbles.

In the unextracted tooth root canal filler 200 of the second embodiment described above, the dental pulp stem cells 220 are transplanted to the apical part of the root canal, and the chemotactic factor 230 is transplanted to the tooth crown part of the root canal. However, the present disclosure is not limited to this example, and the dental pulp stem cells 220 and the chemotactic factor 230 may be uniformly mixed in the entire unextracted tooth root canal filler 200. In such an unextracted tooth root canal filler 200, dental tissues can also be regenerated in a tooth with a complete apical closure, without internal resorption and external resorption and odontoclast differentiation, and odontoblasts are aligned along the dentinal wall.

This unextracted tooth root canal filler 200 can be obtained by, for example, uniformly mixing dental pulp stem cells, a chemotactic factor, and a type I and III collagen mixture (e.g., collagen XYZ, Nitta Gelatin) without formation of bubbles.

EXAMPLES

First Example

[Fractionation and Characterization of Cells]

Human dental pulp was extracted, and digested with collagenase at 37° C. for one hour and a half for isolation of dental pulp cells. Then, the cells were dispersed in DMEM containing 2% serum at a concentration of 1×10⁶ cells/ml, and labeled using CXCR4 antibodies at 4° C. for 30 minutes. Thereafter, flow cytometry was performed. The CXCR4-positive cells derived from human dental pulp represented 20% of the total cells.

Table 1 shows the results of the flow cytometry. Regarding CD29 and CD44, the percentage of CXCR4-positive cells was 90% or more, in the same manner as that of CD105-positive cells. Regarding CD105, the percentage of CD105-positive cells was 90.0%, but the percentage of CXCR4-positive cells was 1.7%. Regarding CD146, CXCR4-positive cells showed a percentage as low as CD105-positive cells. Regarding CD150, which is a marker of further undifferentiated stem cells, the percentage of CXCR4-positive cells was slightly higher than that of CD105-positive cells.

TABLE 1

|  | Canine dental pulp CXCR4-positive cells | Canine dental pulp CD105-positive cells | Canine total dental pulp cells |
| --- | --- | --- | --- |
| CD29 | 99.4% | 90.6% | 95.6% |
| CD34 | 61.6% | 45.5% | 47.1% |
| CD44 | 99.8% | 96.2% | 99.9% |
| CD90 | 0.5% | 0.6% | 1.6% |

TABLE 1-continued

|  | Canine dental pulp CXCR4-positive cells | Canine dental pulp CD105-positive cells | Canine total dental pulp cells |
| --- | --- | --- | --- |
| CD105 | 1.7% | 90.0% | 4.6% |
| CD146 | 0.5% | 0.8% | 0.9% |
| CD150 | 3.6% | 2.3% | 0.9% |
| MHC class I | 82.8% | 36.0% | 73.8% |

In Real-time RT-PCR, CXCR4-positive cells derived from dental pulp and CD105-positive cells derived from dental pulp are compared with respect to RNA expression using primers shown in Tables 2 and 3. This comparison demonstrates that the vascular endothelial growth factor (VEGF)-A shows substantially the same amount of expression in both types of the cells. Expression of cytokine GM-CSF is 2.5 times higher in the CXCR4-positive cells than that in the CD105-positive cells, and expression of the neurotrophic factor NGF in the CD105-positive cells is 2.0 times higher than that in the CXCR4-positive cells. Expression of Neuropeptide Y, Neurotrophine 3, and BDNF in the CXCR4-positive cells is slightly higher than that in the CD105-positive cells. The stem cell marker, SOX2, is expressed higher in the CXCR4-positive cells compared with the CD105-positive cells. Stat3 and Rex1 are expressed similarly between the CXCR4-positive cells and the CD105-positive cells.

TABLE 2

| Gene | | 5'←DNA Sequence→3' | SEQ ID NO | Product size | Accession number |
| --- | --- | --- | --- | --- | --- |
| CXCR4 | Forward | CTGTGGCAAACTGGTACTTC | 1 | 210 bp | NM_001 048026 |
|  | Reverse | TCAACAGGAGGGCAGGTATC | 2 | | |
| Sox2 | Forward | AGCTAGTCTCCAAGCGACGA | 3 | 193 bp | XM_545 216 |
|  | Reverse | CCACGTTTGCAACTGTCCTA | 4 | | |
| Stat3 | Forward | GTGGTGACGGAGAAGCAACA | 5 | 191 bp | XM_844 672 |
|  | Reverse | TTCTGTCTGGTCACCGACTG | 6 | | |
| Bmi1 | Forward | CACTCCCGTTCAGTCTCCTC | 7 | 150 bp | XM_544 225 |
|  | Reverse | CCAGATGAAGTTGCTGACGA | 8 | | |
| Rex1 | Forward | TGGACACGTCCGTGCTCTTC | 9 | 168 bp | XM_533 958 |
|  | Reverse | CTCGGATCTTCCAGATCACC | 10 | | |
| MMP3 | Forward | CCCTCTGATTCCTCCAATGA | 11 | 210 bp | AY1831 43 |
|  | Reverse | GGATGGCCAAAATGAAGAGA | 12 | | |
| VEGF-A | Forward | CTACCTCCACCATGCCAAGT | 13 | 183 bp | NM_001 003175 |
|  | Reverse | ACGCAGGATGGCTTGAAGAT | 14 | | |
| GM-CSF | Forward | GCAGAACCTGCTTTTCTTGG | 15 | 195 bp | S49738 |
|  | Reverse | CCCTCAGGGTCAAACACTTC | 16 | | |
| SDF-1 | Forward | GCCATGAACGCCAAGGTC | 17 | 270 bp | DQ1827 00 |
|  | Reverse | CTTGTTTTAGAGCTTTCTCCAGGT | 18 | | |
| NGF | Forward | CAACAGGACTCACAGGAGCA | 19 | 156 bp | XM_540 250 |
|  | Reverse | ATGTTCACCTCTCCCAGCAC | 20 | | |
| BDNF | Forward | GTTGGCCGACACTTTTGAAC | 21 | 202 bp | NM_001 002975 |
|  | Reverse | CCTCATCGACATGTTTGCAG | 22 | | |
| Neuropeptide Y | Forward | ATCACCAGGCAGAGGTATGG | 23 | 206 bp | XM_532 492 |
|  | Reverse | TTGGGAGGATAGGCAGATTC | 24 | | |
| Neurotrophin 3 | Forward | CCCCCTCCCTTGTATCTCAT | 25 | 311 bp | XM_532 492 |
|  | Reverse | CGTAGGTTTGGGACGTTTTG | 26 | | |

TABLE 2-continued

| Gene | | 5'←DNA Sequence→3' | SEQ ID NO | Product size | Accession number |
|---|---|---|---|---|---|
| E-selectin | Forward | GTATGTGCGTTTGCATGTCC | 27 | 195 bp | L23087 |
| | Reverse | CAGGAGCCAGAGGAGAAATG | 28 | | |
| VCAM-1 | Forward | GGGATTAACCAGGCTGGAAT | 29 | 190 bp | CFU320186 |
| | Reverse | TGTCTCCCGTCTCTGCTTTT | 30 | | |
| Rhombotin-2 | Forward | GGCGCCTCTACTACAAGCTG | 31 | 199 bp | XM_846184 |
| | Reverse | TATCTGTCGCCCACACAGAA | 32 | | |

TABLE 3

| Gene | | 5'←DNA Sequence→3' | SEQ ID NO | Product size | Accession number |
|---|---|---|---|---|---|
| ECSCR | Forward | CCCCAGGTGTTATCAGCTTC | 33 | 169 bp | XM_549577 |
| | Reverse | TCTTTCTCTCCGTTGGCTGT | 34 | | |
| SLC6A6 | Forward | CACGTCCTTGGTCGATCTTT | 35 | 188 bp | NM_001003311 |
| | Reverse | AGAATGCAACCCACAAAAGG | 36 | | |
| ap2 | Forward | CGGATGACAGAAAAGTCAAG | 37 | 194 bp | XM_543759 |
| | Reverse | TTCAGCTTGATGTCCCTTGG | 38 | | |
| Neurofilament | Forward | GCTGGACCGACTATCAGAGG | 39 | 196 bp | NM_001003352 |
| | Reverse | CTGGTAGGATGCGATGTCAG | 40 | | |
| Neuromodulin | Forward | ACAAGATGGCATCAAACCAG | 41 | 181 bp | XM_535747 |
| | Reverse | CTTCTTCTCCAGGCCATCAG | 42 | | |
| Enamelysin | Forward | TATTCACCGTTGCTGCTCAC | 43 | 151 bp | XM_849546 |
| | Reverse | TACAATGCCTGGATCCCTTT | 44 | | |
| Osteocalcin | Forward | GGCAGCGAGGTGGTGAGGAG | 45 | 180 bp | AF205942 |
| | Reverse | CTAGACCGGGCCATAGAAG | 46 | | |
| DSPP | Forward | GTCCTAGTGGGAATGGAGCA | 47 | 190 bp | XM_544971 |
| | Reverse | TCTTCAGGGCCATCATCTTC | 48 | | |
| Axin2 | Forward | GAAAGGGTCAGGTCACCAAA | 49 | 190 bp | XM_548025 |
| | Reverse | CATTTGTCCCTCTCCAGGAA | 50 | | |
| Periostin | Forward | AAACCATTGGAGGCAAACAG | 51 | 209 bp | XM_534490 |
| | Reverse | TGCAGCTTCAAGTAGGCTGA | 52 | | |
| PLAP-1 | Forward | TCCCGTCAGGATTACAGGAG | 53 | 210 bp | XM_848228 |
| | Reverse | GAACGCTCATTCTGCTCACA | 54 | | |
| Tenascin-C | Forward | TGGCTGTCTTGGACACAGAG | 55 | 181 bp | XM_538811 |
| | Reverse | GACTCCAGAGTTGGGGTCTG | 56 | | |
| Syndecan 3 | Forward | TCATGCAGGACAGCTTCAAC | 57 | 186 bp | XM_544449 |
| | Reverse | AGGGCTGGAATCTAGGGAAA | 58 | | |
| collagen α1(I) | Forward | CTTCCTGGAATGAAGGGACA | 59 | 205 bp | NM_001003090 |
| | Reverse | CAGTAGCACCATCGTTTCCA | 60 | | |
| collagen α1(III) | Forward | AGGGTCCTGCTGGAAAGAAT | 61 | 199 bp | XM_857956 |
| | Reverse | GGAACTCCAGGTGAACCAGA | 62 | | |
| β-actin | Forward | AAGTACCCCATTGAGCACGG | 63 | 257 bp | Z70044 |
| | Reverse | ATCACGATGCCAGTGGTGCG | 64 | | |

[Regeneration of Canine Dental Pulp after Pulpectomy]

Regeneration of canine dental pulp after transplantation of CD105-positive cells and CXCR4-positive cells in the pulpectomized root canal will be described hereinafter.

Figure 6A:
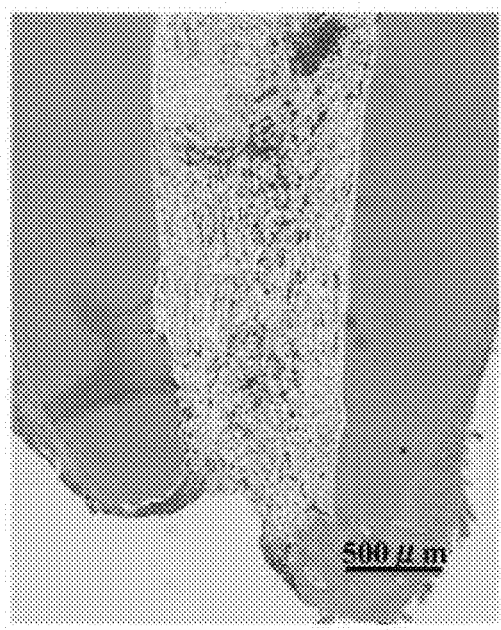
FIG. 6A is a photograph showing a root canal after 14 days from replantation in which the root canal of an extracted tooth was enlarged in vitro after pulpectomy, SDF-1 and CD105-positive cells were absorbed in a type I and III collagen mixture, and a filer was injected into the root canal.
Figure 6B:
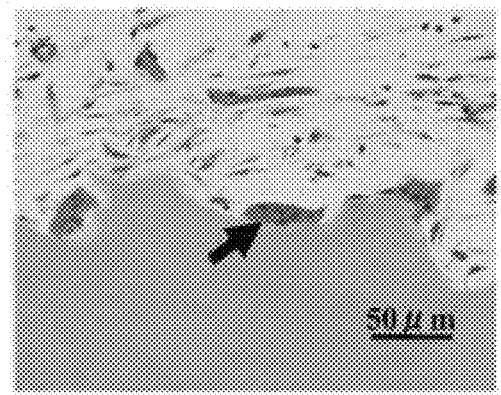
FIG. 6B is a magnified photograph showing a dentinal wall in a root canal after 14 days from replantation in which the root canal of an extracted tooth was enlarged in vitro after pulpectomy, SDF-1 and CD105-positive cells were absorbed in a type I and III collagen mixture, and a filer was injected into the root canal.
Figure 6C:
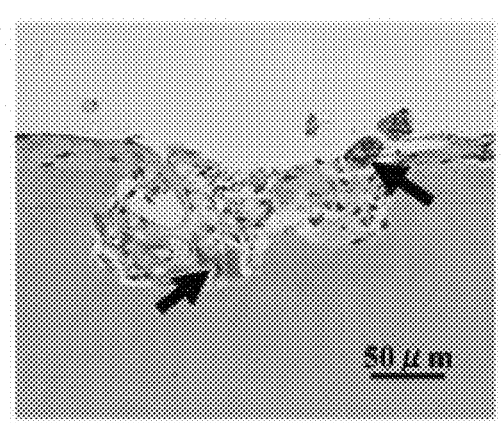
FIG. 6C is a magnified photograph showing dentin and cementum walls at the outside of a root 14 days after replantation in which the root canal of an extracted tooth was enlarged in vitro after pulpectomy, SDF-1 and CD105-positive cells were absorbed in a type I and III collagen mixture, and a filer was injected into the root canal.

CD105-positive cells and CXCR4-positive cells were fractionated from canine dental pulp tissues. Specifically, 40 μl of collagen XYZ (Nitta Gelatin, a type I and III collagen mixture) including SDF-1 (200 ng) was first absorbed into a tip of Pipetman, and 20 μl of collagen XYZ (Nitta Gelatin, a type I and III collagen mixture) including 1×10$^6$ CD 105-positive cells was then absorbed, to a total amount of 60 μl. In this manner, a root canal filler to be injected into a root canal of an extracted tooth was formed. After extraction of a canine upper-jaw anterior tooth, dental pulp was completely removed and the root canal was enlarged to #70 in a culture medium, thereby enlarging the width of the root canal in the apical portion to 0.7 mm or more. Then, within 30 minutes after the dental pulp removal, the above root canal filler was injected into a site corresponding to a region where the dental pulp in the root canal originally existed. The tooth was replanted in the canine tooth extraction socket within 30 minutes, and the upper part of the tooth was sealed with phosphate cement and a chemically polymerized resin. The tooth was extracted for preparation of a paraffin sample after 14 days. FIG. 6A shows the results. FIG. 6B is a magnified photograph showing the dentinal wall in the root canal. FIG. 6C is a magnified photograph showing dentinal and cementum walls outside of the root of a tooth. FIGS. 6A, 6B, and 6C are photographs after H-E staining.

Figure 7A:
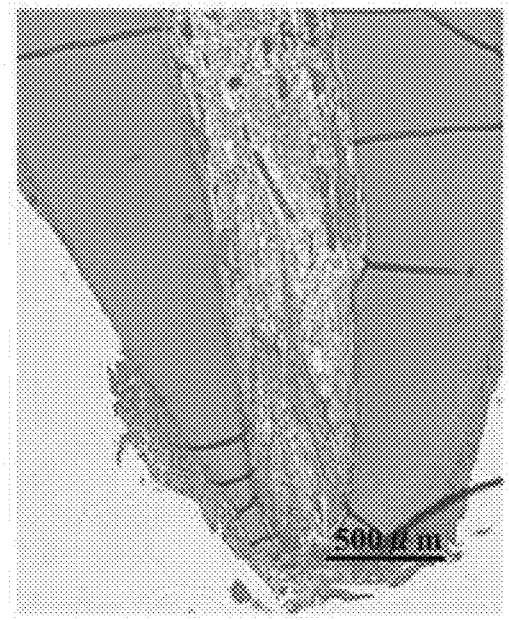
FIG. 7A is a photograph showing a root canal without extraction 14 days after injection of a filter composed of SDF-1 and CD105-positive cells in a type I and III collagen mixture into the pulpectomized and enlarged root canal in vivo.
Figure 7B:
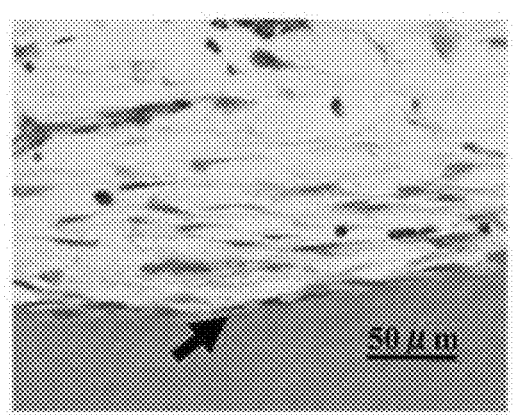
FIG. 7B is a magnified photograph showing a dentinal wall in a root canal without extraction 14 days after injection of a filter composed of SDF-1 and CD105-positive cells in a type I and III collagen mixture into the pulpectomized and enlarged root canal in vivo.

Then, 13 µl of collagen XYZ (Nitta Gelatin, a type I and III collagen mixture) including SDF-1 (200 ng) was first absorbed into a tip of Pipetman, and 7 µl of collagen XYZ (Nitta Gelatin, a type I and III collagen mixture) including 1×10$^6$ CD105-positive cells was then absorbed, to a total amount of 20 µl. In this manner, an unextracted tooth root canal filler 200 was obtained. In this unextracted tooth root canal filler 200, SDF-1 was transplanted to ⅔ of the tooth crown part of the root canal, and CD105-positive cells were transplanted to ⅓ of the apical part of the root canal. Without extraction of the canine upper-jaw anterior tooth, dental pulp was removed and the root canal was enlarged to #70, and the width of the root canal in the apical area was enlarged to 0.7 mm or more. Then, within 30 minutes after the dental pulp removal, the unextracted tooth root canal filler 200 was injected into a site corresponding to a region where the dental pulp in the root canal originally existed. The upper part of the tooth was sealed with phosphate cement and a chemically polymerized resin within 30 minutes. The tooth was extracted for preparation of a paraffin sample after 14 days. FIG. 7A shows the results. FIG. 7B is a magnified photograph showing the dentinal wall in the root canal. FIGS. 7A and 7B are photographs after H-E staining.

Figure 8A:
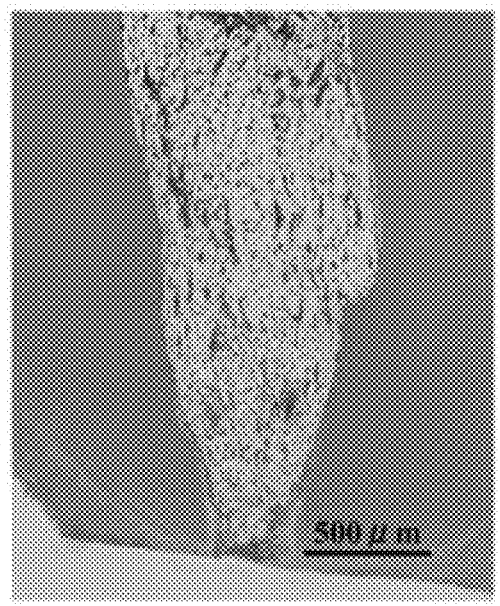
FIG. 8A is a photograph showing a root canal without extraction 14 days after injection of a filter composed of SDF-1 and CXCR4-positive cells in a type I and III collagen mixture into the pulpectomized and enlarged root canal in vivo.
Figure 8B:
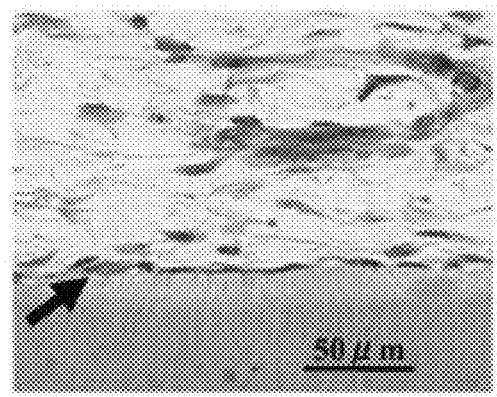
FIG. 8B is a magnified photograph showing a root canal without extraction 14 days after injection of a filter composed of SDF-1 and CXCR4-positive cells in a type I and III collagen mixture into the pulpectomized and enlarged root canal in vivo.

Then, 13 µl of collagen XYZ (Nitta Gelatin, a type I and III collagen mixture) including SDF-1 (200 ng) was first absorbed into a tip of Pipetman, and 7 µl of collagen XYZ (Nitta Gelatin, a type I and III collagen mixture) including 1×10$^6$ CXCR4-positive cells was then absorbed, to a total amount of 20 µl. In this manner, an unextracted tooth root canal filler 200 was obtained. In this unextracted tooth root canal filler 200, SDF-1 was transplanted to ⅔ of the tooth crown part of the root canal, and CXCR4-positive cells were transplanted to ⅓ of the apical part of the root canal. Without extraction of the canine upper-jaw anterior tooth, dental pulp was removed and the root canal was enlarged to #70, and the width of the root canal in the apical area was enlarged to 0.7 mm or more. Then, within 30 minutes after the dental pulp removal, the unextracted tooth root canal filler 200 was injected into a site corresponding to a region where the dental pulp in the root canal originally existed. The upper part of the tooth was sealed with phosphate cement and a chemically polymerized resin within 30 minutes. The tooth was extracted for preparation of a paraffin sample after 14 days. FIG. 8A shows the results. FIG. 8B is a magnified photograph showing the dentinal wall in the root canal. FIGS. 8A and 8B are photographs after H-E staining.

In the newly regenerated dental pulp tissues, blood clots remained and inflammation was slightly observed in the case of tooth extraction (FIGS. 6A-6C), as compared to the case of tooth unextraction (FIGS. 7A, 7B, 8A, and 8B). In particular, FIG. 6A shows clots in an upper part, in the drawing sheet, of regenerated dental pulp tissues, and a large number of small clots scattered in the entire regenerated dental pulp tissues. In addition, odontoclasts were observed in the dentinal wall in the root canal in the case of tooth extraction, and internal resorption was observed (see FIG. 6B). External resorption was also observed in the dentin and the cementum outside of the tooth root (see FIG. 6C). Both of the internal resorption and the external resorption do not cause disorder in daily life as long as the resorptions are mild and finished. However, when the resorption highly progresses, dental agitation or loss of a tooth is more likely to occur, and the risk of caries or periodontal disease increases.

On the other hand, in the case of tooth unextraction, no odontoclasts were observed in the dentinal wall in the root canal, none of internal resorption and external resorption was observed, and odontoblasts were aligned along the dentinal wall (see FIGS. 7B and 8B). No significant differences in the degree of newly formed blood capillaries, nerves, and specific dental pulp tissues were observed between transplantation of CD105-positive cells and transplantation of CXCR4-positive cells, as dental pulp stem cells.

The foregoing results proved that the case of injecting the filler into the root canal of an unextracted tooth is more advantageous for dental pulp regeneration than the case of injecting the filler into the root canal of an extracted tooth. In addition, it is also concluded that transplantation of CXCR4-positive cells derived from dental pulp are also effective on dental pulp regeneration, to the same degree as that of CD105-positive cells.

Second Example

Then, in a second example, potential of the dental tissue regeneration of the unextracted tooth root canal filler will be more specifically examined.

[Cell Fractionation with Flow Cytometry]

Dental pulp cells were isolated from an upper canine. Primary adipocytes were isolated from adipose tissues of the same canine as control. The cells were subjected to immunostaining as mouse IgG1-negative control (W3/25) (AbD Serotec Ltd., Oxford, UK). The cells were subjected to immunostaining with mouse IgG1-negative control (Phyco-erythrin, PE) (MCA928PE) (AbD Serotec) and mouse anti-human CD105 (PE) (43A3) (BioLegend, San Diego, Calif., USA) at 4° C. for 90 minutes. The resultant cells were incubated in 2 µg/ml of a propidium iodide-containing HEPES buffer (Sigma), and subjected to fractionation with JSAN (Bay Bioscience, Kobe, Japan). CD105-positive cells and CD105-negative cells derived from dental pulp and adipose tissues, and total pulp cells without cell fractionation were plated on a 35-mm collagen type I coated dish (Asahi Technoglass Corp., Funabashi, JAPAN), and cultured in EBM2 (Cambrex Bio Science, Walkersville, Md., USA) supplemented with 10 ng/ml of IGF (Cambrex Bio Science), 5 ng/ml of EGF (Cambrex Bio Science), and 10% fetal bovine serum (Invitrogen Corporation, Carlsbad, Calif., USA) to maintain the phenotype of the cells. The culture medium was replaced with a fresh medium once in four or five days. After reaching 60-70% confluence, the cells were detached at 37° C. for 10 minutes in 0.02% EDTA. Then, the cells were subcultured with a 1:4 dilution.

Dental pulp CD105-positive cells were further characterized at the third passage of culture, and were compared with adipose CD105-positive cells and unfractionated total dental pulp cells. The cells were stained with mouse IgG1 negative control (AbD Serotec Ltd.), mouse IgG1 negative control (fluoresceinisothiocyanate, FITC) (MCA928F) (AbD Serotec), mouse IgG1 negative control (Phycoerythrin-Cy5,PE-Cy5) (MCA928C) (AbD Serotec), mouse IgG1 negative control (Alexa 647) (MRC OX-34) (AbDSerotec), and antibodies to CD24 (Alexa Fluor 647) (ML5) (BioLegend), CD29 (PE-Cy5) (MEM-101A) (eBioscience), CD31 (FITC) (Qbend10) (Dako), CD33 (FITC) (HIM3-4) (BD Bioscience), CD34 (Allophycocyanin, APC) (1H6) (R&D Systems, Inc., Minneapolis, Minn., USA), CD44 (Phycoerythrin-Cy7, PE-Cy7) (IM7) (eBioscience), CD73 (APC) (AD2) (BioLegend), CD90 (FITC) (YKIX337.217) (AbD Serotec), CD146 (FITC) (sc-18837) (Santa Cruz, Biotech, Santa Cruz, Calif., USA), CD150 (FITC) (A12) (AbD Serotec), MHC class I (R-PE) (3F10) (Ancell Corporation, Bayport, Minn., USA), MHC class II (APC) (TDR31.1) (Ancell), and CXCR4 (FITC) (12G5) (R&D).

[Expression Analysis of Stem Cell Marker, Angiogenic Factor and Neurotrophic Factor by Real-Time RT-PCR]

To further characterize the phenotype of the cell populations, total RNA was extracted from dental pulp and adipose CD105-positive cells and total dental pulp cells at the third passage of culture, using Trizol (Invitrogen). In each experiment, the number of these cells was normalized to $5 \times 10^4$ cells in each experiment. First-strand cDNA was synthesized from total RNA using ReverTra Ace-α (Toyobo, Tokyo, Japan). Real-time RT-PCR amplifications were performed using stem cell markers, canine CXCR4, Sox2, Stat3, Bmi1, and Rex1 (Tables 2 and 3), labeled with Light Cycler-Fast Start DNA master SYBR Green I (Roche Diagnostics). at 95° C. for 10 seconds, at 62° C. for 15 seconds, and 72° C. for 8 seconds in Light Cycler (Roche Diagnostics, Pleasanton, Calif.). The design of the oligonucleotide primers was based on published canine cDNA sequences. When canine sequences were not available, human sequences were used. To study mRNA expression of angiogenic and neurotrophic factors, real-time RT-PCR amplifications of canine matrix metalloproteinase (MMP)-3, VEGF-A, a granulocyte-monocytecolony-stimulating factor (GM-CSF), SDF-1, NGF, BDNF, Neuropeptide Y, Neurotrophin 3, E-selectin, VCAM1, rhombotin 2, ECSCR, and SLC6A6 were also performed. The RT-PCR products were confirmed by sequencing based on published cDNA sequences. The expression in dental pulp CD105-positive cells and adipose CD105-positive cells was compared with that in total dental pulp cells at the third passage of culture after normalizing with β-actin.

[Proliferation and Migration Analysis]

First, $10^3$ dental pulp CD105-positive cells were inoculated in a 96-well plate in EBM2 supplemented with 0.2% bovine serum albumin (Sigma) and SDF-1 (50 ng/ml). Then, the proliferation potential of the dental pulp CD105-positive cells in response to stromal cell-derived factor-1(SDF-1) (Acris, Herford, Germany) was compared with those of total dental pulp cells and adipose CD105-positive cells at the fourth passage of culture. Thereafter, 10 µl of Tetra-color one (registered trade name, Seikagaku Kogyo, Co., Tokyo, JAPAN) was added to the 96-well plate, and the number of cells was measured at 2, 12, 24, and 36 hours of culture using a spectrophotometer at an absorbance of 450 nm Wells containing no cells served as negative controls.

The migration potential of dental pulp CD105-positive cells in response to SDF-1 was compared with those of total dental pulp cells and adipose CD105-positive cells by a horizontal chemotaxis assay. A real-time horizontal chemotaxis assay was performed using TAXIScan-FL (Effector Cell Institute, Tokyo, JAPAN). In the TAXIScan-FL, a channel optimized to the cell size was formed between silicon with 6-µm holes and a glass plate, and 1 µl of cells ($10^5$ cells/ml) was placed in one end of the channel, and 10 ng/µl of SDF-1 was placed in the other end of the channel with a constant concentration gradient. Then, video images of cell migration were taken with a microscope for 6 hours.

[Fractionation and Characterization of CD105-Positive Cells Derived from Dental Pulp and Adipose]

Figure 9A:
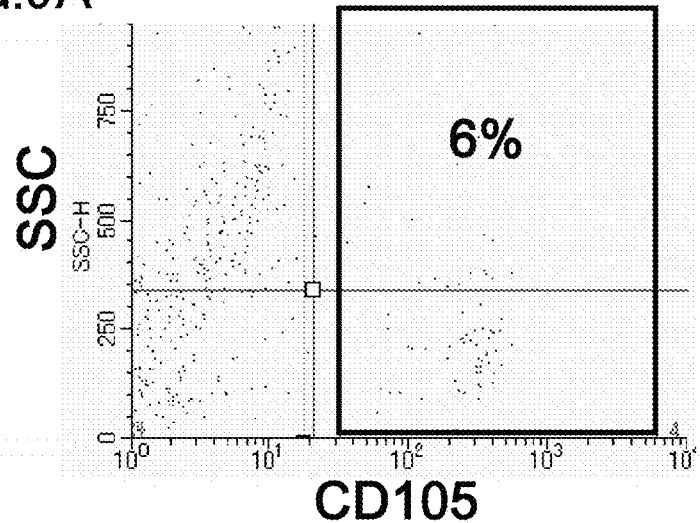
FIG. 9A is a view showing the percentage of CD105-positive cells in dental pulp cells isolated from canine permanent tooth pulp tissues by flow cytometry.
Figure 9B:
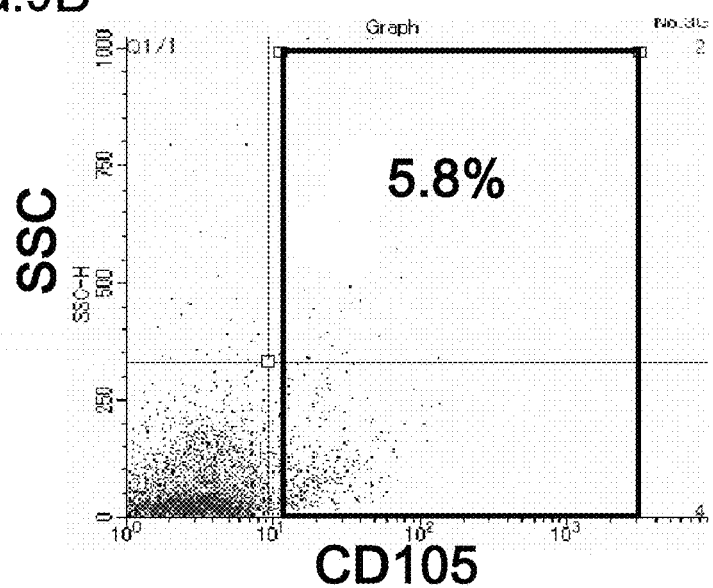
FIG. 9B is a view showing the percentage of CD105-positive cells in adipose cells isolated from canine adipose tissues by flow cytometry.
Figure 9C:
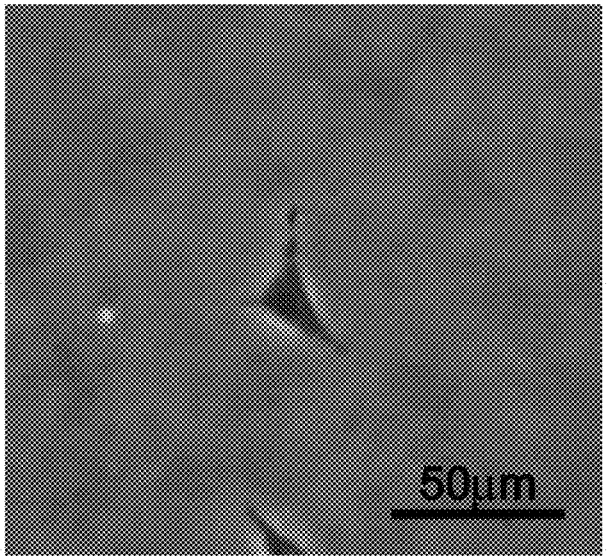
FIG. 9C is a photograph showing primary dental pulp CD105-positive cells on the third day of culture isolated from canine permanent tooth pulp tissues.
Figure 9D:
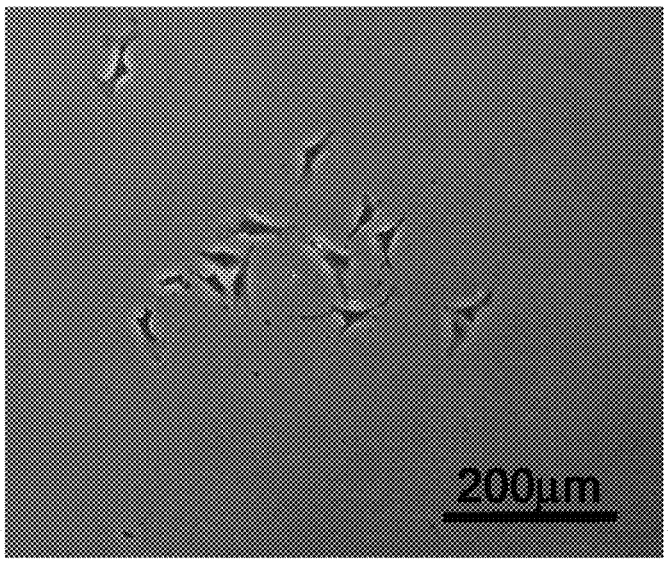
FIG. 9D is a photograph showing primary dental pulp CD105-positive cells on the tenth day of culture isolated from canine permanent tooth pulp tissues.
Figure 9E:
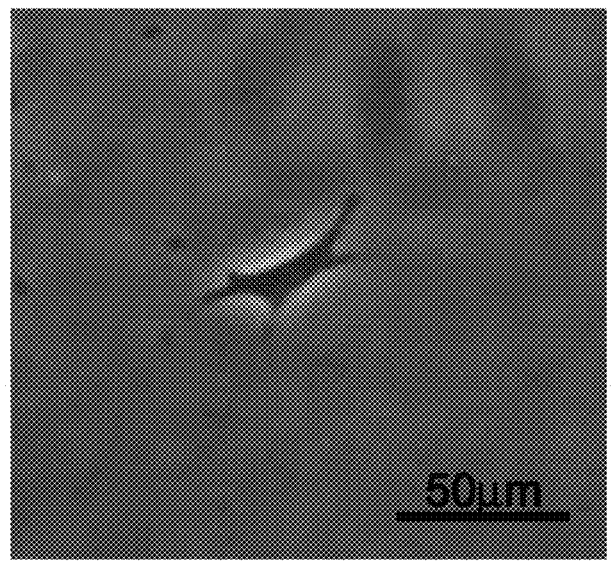
FIG. 9E is a photograph showing primary adipose CD105-positive cells on the third day of culture isolated from adipose tissues.
Figure 9F:
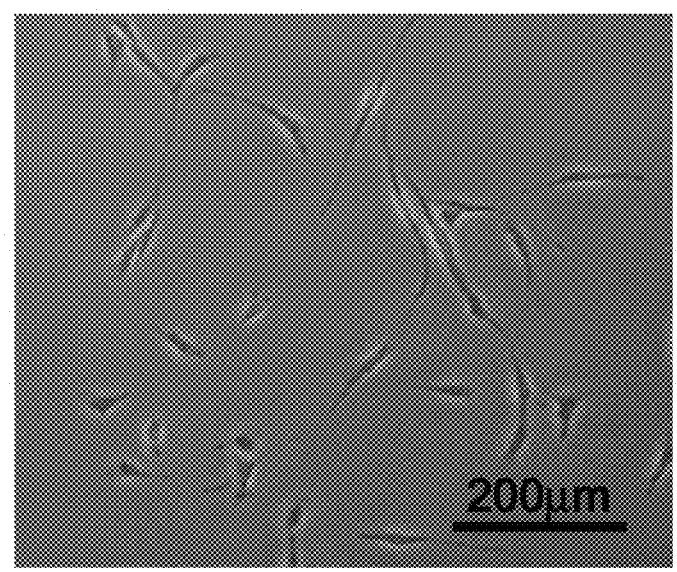
FIG. 9F is a photograph showing primary adipose CD105-positive cells on the tenth day of culture isolated from adipose tissues.

As shown in FIGS. 9A and 9B, dental pulp CD105-positive cells isolated from canine permanent pulp tissues by flow cytometry using CD105 antibodies and adipose CD105-positive cells derived from adipose tissues of the same individual represented 6% and 5.8% of total cells, respectively. As shown in FIGS. 9C, 9D, 9E, and 9F, the dental pulp and adipose CD105-positive cells both were stellate with long processes. Although not shown, dental pulp CD105-negative cells had irregularly shaped short projections. EBM2 supplemented with IGF1, EGF, and 10% fetal calf serum maintained the phenotype of CD105-positive cells, demonstrating more than 98% at the sixth passage of culture. When single CD105-positive cells were plated in a 35-mm collagen type I coated dish, colonies were formed in 10 days, demonstrating a colony formation potential of these CD105-positive cells. The efficiency of attachment and proliferation of dental pulp and adipose CD105-positive cells and dental pulp CD105-negative cells were 8%, 3.7%, and 1%, respectively. Limiting dilution analysis at the third passage of culture showed that the frequency of a colony-forming unit (CFU) was estimated to be 80% in dental pulp CD105-positive cells, and 30% in total dental pulp cells, and 50% in adipose CD105-positive cells.

To characterize dental pulp CD105-positive cells, flow cytometry was performed using cell surface antigen markers, and dental pulp CD105-positive cells were compared with adipose CD105-positive cells and total dental pulp cells. The dental pulp CD105-positive cells, the adipose CD105-positive cells, and the total dental pulp cells were at the third passage of culture, CD29, CD44, CD90, and CD105 were positive, and CD31 was negative. As shown in Table 4 below, it is notable that the dental pulp CD105-positive cells expresses CD73, CD150, and CXCR4 more strongly than the adipose CD105-positive cells and the total dental pulp cells.

TABLE 4

|  | Dental pulp CD105-positive cells | Adipose CD105-positive cells | Total dental pulp cells |
| --- | --- | --- | --- |
| CD24 | 1.8% | 1.7% | 0.3% |
| CD29 | 95.9% | 90.5% | 99.2% |
| CD31 | 0% | 0% | 0% |
| CD33 | 3.7% | 0% | 0.2% |
| CD34 | 45.5% | 0.1% | 47.1% |
| CD44 | 96.2% | 92.3% | 99.9% |
| CD73 | 97.2% | 0.8% | 22.3% |
| CD90 | 98.1% | 95.6% | 97.5% |
| CD105 | 98.5% | 74.0% | 4.6% |
| CD146 | 0.8% | 0.2% | 0.9% |
| CD150 | 2.3% | 0.2% | 0.9% |
| MHC class I | 36.0% | 80.0% | 73.8% |
| MHC class II | 0.4% | 0% | 0.4% |
| CXCR4 | 12.2% | 5.9% | 5.3% |

In the dental pulp CD105-positive cells, stem cell markers of, for example, CXCR4, Sox2, and Bmi1 mRNA were expressed 16.8-, 64-, and 3.5-fold, respectively, higher than those in the total dental pulp cells, suggesting the stem properties of the pulp CD105-positive cells. In the dental pulp CD105-positive cells, CXCR4, Sox2, and Bmi1 mRNA were more highly expressed than those in the adipose CD105-positive cells. As shown in Table 5, in the dental pulp CD105-positive cells, angiogenic factors or neurotrophic factors of, for example, VEGF-A, GM-CSF, a nerve growth factor (NGF), a brain-derived neurotrophic factor (BDNF), neuropeptide Y, neurotrophin 3, E-selectin, and VCAM-1 were more highly expressed than those in the adipose CD105-positive cells.

TABLE 5

|  | Dental pulpCD105-positive cells/ total dental pulp cells | Adipose CD105-positive cells/ total dental pulp cells |
| --- | --- | --- |
| CXCR4 | 16.8 | 7.0 |
| Sox2 | 64.0 | 16.0 |
| Stat3 | 0.8 | 0.1 |
| Bmi1 | 3.5 | 0.1 |
| Rex1 | 0.9 | 1.9 |
| MMP3 | 26.1 | 11.6 |
| VEGF-A | 3.6 | 1.6 |
| GM-CSF | 5.8 | 1.9 |
| SDF-1 | 1.7 | 1.8 |
| NGF | 4.1 | 0.5 |
| BDNF | 16.0 | 0.5 |
| Neuropeptide Y | 5.2 | 0.1 |
| Neurotrophin 3 | 5.3 | 0.2 |
| E-selectin | 18.1 | 1.1 |
| VCAM-1 | 54.6 | 18.7 |
| Rhombotin-2 | 23.8 | 1.7 |
| ECSCR | 28.5 | 0.8 |
| SLC6A6 | 12.7 | 1.5 |

[Multipotency In Vitro]

Dental pulp CD105-positive cells at the third through fifth passages of culture were differentiated into adipose, blood vessels, nerves, and dentin/bones by induction, and were compared with adipose CD105-positive cells and unfractionated dental pulp cells.

Figure 10A:
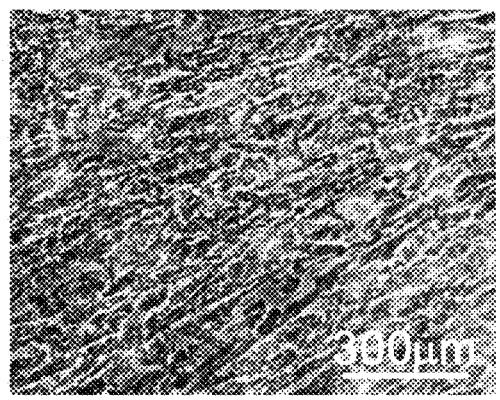
FIG. 10A is a photograph showing the adipogenic induction of dental pulp CD105-positive cells on the 30th day.
Figure 10B:
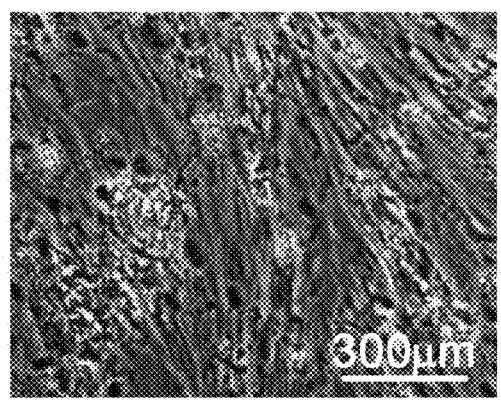
FIG. 10B is a photograph showing the adipogenic induction of unfractionated total dental pulp cells on the 30th day.
Figure 10C:
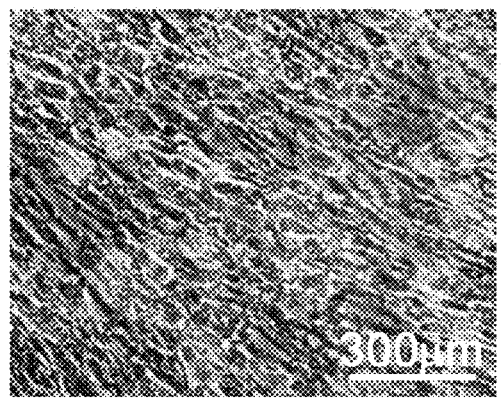
FIG. 10C is a photograph showing the adipogenic induction of adipose CD105-positive cells on the 30th day.
Figure 10D:
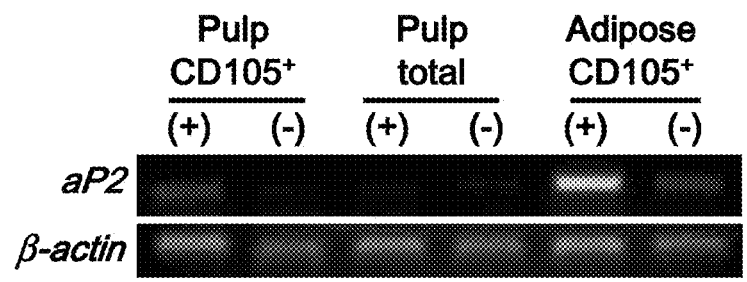
FIG. 10D shows a comparison of gene expression of the adipogenic induction among dental pulp CD105-positive cells, unfractionated total dental pulp cells, and adipose CD105-positive cells.
Figure 10E:
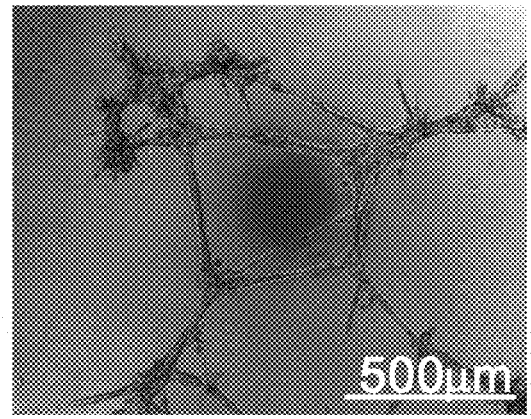
FIG. 10E is a photograph showing the angiogenic induction of dental pulp CD105-positive cells after 12 hours.
Figure 10F:
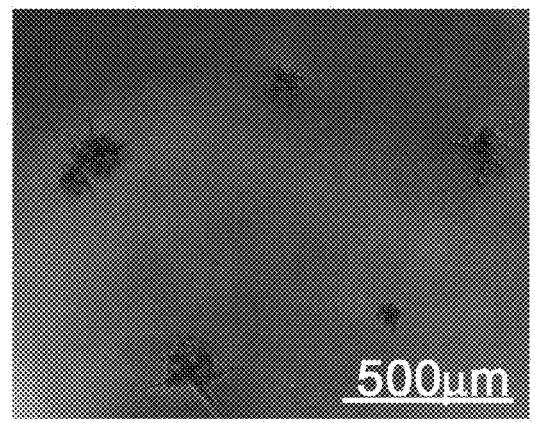
FIG. 10F is a photograph showing the angiogenic induction of unfractionated total dental pulp cells after 12 hours.
Figure 10G:
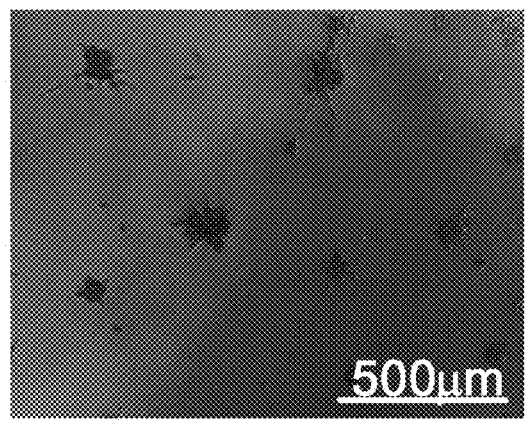
FIG. 10G is a photograph showing the angiogenic induction of adipose CD105-positive cells after 12 hours.
Figure 10H:
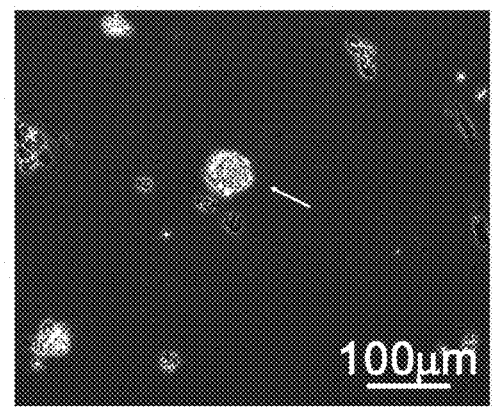
FIG. 10H is a photograph showing potential of the neurosphere formation of dental pulp CD105-positive cells on the 14th day.
Figure 10I:
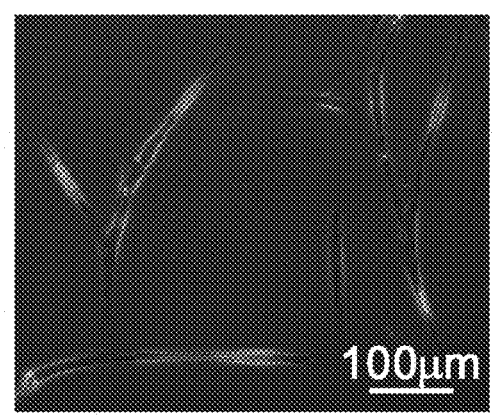
FIG. 10I is a photograph showing potential of the neurosphere formation of unfractionated total dental pulp cells on the 14th day.
Figure 10J:
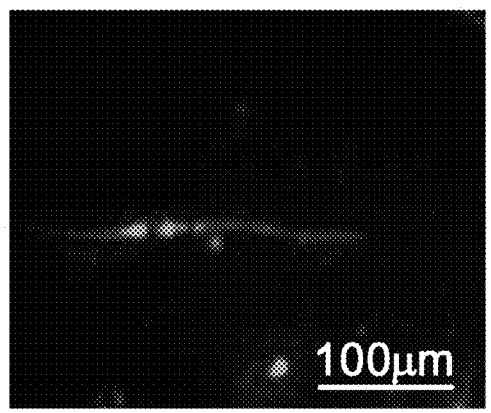
FIG. 10J is a photograph showing the neurogenic induction of dental pulp CD105-positive cells immunostained with neurofilament on the 28th day.
Figure 10K:
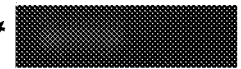
FIG. 10K shows mRNA expression of neurofilament, neuromodulin, voltage-dependent sodium channel, type Ia (Scn1A) and β-actin in dental pulp CD105-positive cells.
Figure 10K:
Figure 10K:
Figure 10K:
Figure 10L:
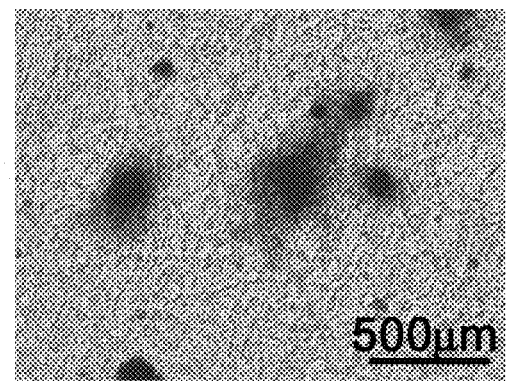
FIG. 10L is a photograph showing the dentinogenic/osteogenic induction of dental pulp CD105-positive cells on the 28th day.

As shown in FIGS. 10A and 10D, the dental pulp stem cells showed differentiation potential to adipose cells. As shown in FIG. 10E, the dental pulp stem cells showed differentiation potential to vascular endothelial cells. As shown in FIGS. 10H, 10J, and 10K, the dental pulp stem cells showed differentiation potential to neuronal cells. As shown in FIGS. 10L and 10O, the dental pulp stem cells showed differentiation potential to odontoblast/osteoblast lineage.

Figure 10P:
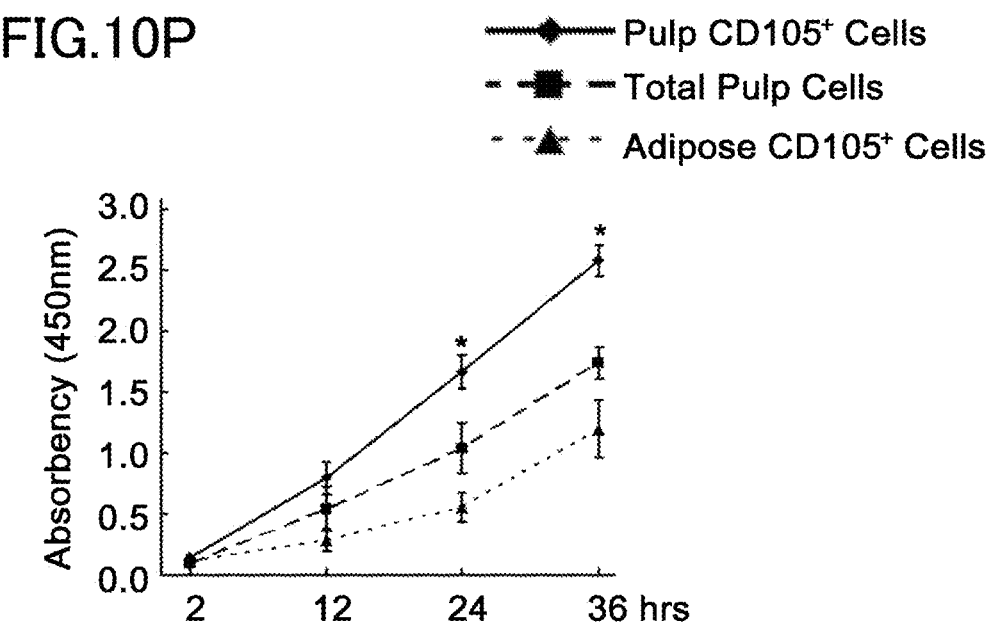
FIG. 10P is a graph showing the proliferation activity of dental pulp CD105-positive cells, unfractionated total dental pulp cells, and adipose CD105-positive cells supplemented with SDF-1 at a final concentration of 50 ng/ml after 2, 12, 24, and 36 hours of culture.

However, as shown in FIGS. 10L and 10M, a larger amount of calcified matrix was observed in the total dental pulp cells than in the dental pulp CD105-positive cells. As shown in FIGS. 10C, 10D, 10N, 10O, and 10G, the adipose CD105-positive cells showed adipogenic induction and osteogenic induction, but did not show angiogenic or neurogenic induction. As shown in FIG. 10P, the proliferation activity by SDF-1 in the dental pulp CD105-positive cells was higher than those in the total dental pulp cells and the adipose CD105-positive cells. In FIG. 10P, data is the average±SD of four samples (where *P<0.01). The experiment was repeated three times, and one representative experiment was presented. As s shown in TAXIScan-FL, the migration activity by SDF-1 in the dental pulp CD105-positive cells was higher than those in the total dental pulp cells and the adipose CD105-positive cells.

[Autologous Transplantation in Root Canal after Pulpectomy of Stem Cells/Progenitor Cells]

The dental pulp was completely removed from a canine (Narc, Chiba, Japan) permanent tooth with a complete apical closure, and an experimental model to which cellular fractions were transplanted to regenerate dental pulp was established. After general anesthesia with sodium pentobarbital (Schering-Plough, Germany), dental pulp was completely removed from the maxillary second incisor and the mandibular third incisor, and the apical foramen was enlarged to 0.7 mm using #70K-file (MANI. INC, Tochigi, Japan). A root canal filler in which dental pulp stem cells were transplanted to the apical part and SDF-1 was transplanted to the tooth crown part using collagen XYZ as an extracellular matrix. Specifically, autologous transplantation of dental pulp CD105-positive cells, adipose CD105-positive cells, or total dental pulp cells, 1×10$^6$ cells in each, from the third to fourth passages of culture after DiI labeling was performed together with collagen XYZ (Nitta Gelatin, Osaka, Japan) into a lower part of the root canals. SDF-1 with a final concentration of 15 ng/µl and collagen XYZ were further transplanted into an upper part of the root canal. The cavity was sealed with zinc phosphate cement (Elite Cement, GC, Tokyo, Japan) and a bonding agent (Clearfil Mega Bond, Kuraray), and then repaired with composite resin (Clearfil HI, Kuraray, Kurashiki, Japan). In this experiment, 60 teeth of 15 canines were used. Samples were prepared after 14 days by injecting dental pulp CD105-positive cells and SDF-1 into 10 teeth, adipose CD105-positive cells and SDF-1 into five teeth, total dental pulp cells and SDF-1 into five teeth, only SDF-1 without cells into five teeth, only dental pulp CD105-positive cells without SDF-1 into five teeth, and only scaffold without cells into five teeth. Dental pulp CD105-positive cells and SDF-1 were injected into six teeth, and a two-dimensional electrophoresis analysis was performed after 28 days. Samples were prepared after 90 days by injecting dental pulp CD105-positive cells with SDF-1, adipose CD105-positive cells with SDF-1, and total dental pulp cells with SDF-1 into four teeth. Seven normal teeth were used as controls. For morphological analysis, the samples were fixed at 4° C. overnight in 4% paraformaldehyde (PFA) (Nakarai Tesque, Kyoto, Japan), decalcified with 10% formic acid, and then embedded in paraffin wax (Sigma). Then, the paraffin sections (with a thickness of 5 µm) were morphologically examined after staining with hematoxylin and eosin (HE).

For blood vessel staining, 5-µm paraffin sections were deparaffinized, stained with Fluorescein Griffonia (Bandeiraea) Simplicifolia Lectin 1/fluorescein-galanthus nivalis (snowdrop) lectin (20 µg/ml, Vector laboratories, Inc., Youngstown, Ohio) for 15 minutes. Then, the presence and localization of transplanted cells in newly formed blood vessels were observed with a fluorescence microscope BIOREVO, BZ-9000 (KEYENCE, Osaka, Japan). Regenerated dental pulp after 14 days from transplantation and normal dental pulp were fixed for 45 minutes in 4% paraformaldehyde, subjected to treatment with PBS containing 0.3% Triton X, subjected to blocking, and then subjected to whole-mount immunostaining at 4° C. for 12 hours with GS-IB4 (Griffoniasimplicifolia, Alexa Fluor 488) lecitin. Three-dimensional photographs of the newly formed blood vessels and the transplanted cells were taken with a microscope FV1000MPE (Olympus).

Staining of newly generated nerves was performed in the following manner. First, 5-µm paraffin sections were deparaffinized, treated with PBS containing 3% Triton X, blocked with 2% goat serum, and primarily stained with PGP-9.5 for 12 hours at 4° C. Then, the sections were washed three times with PBS, and secondary staining was performed with biotinylatedgoat anti-rabbit IgG (Vector) (1:200) for one hour at room temperature. Then, the sections were treated with an ABC reagent (VectorLaboratories, Burlingame, Calif.), and color was developed with DAB for 10 minutes.

To confirm connection of a newly formed nerve projection to an inferior alveolar nerve, dental pulp CD105-positive cells without DiI labeling, were transplanted into the mandibular third incisor, and DiI was applied onto regenerated dental pulp on day 14 after transplantation. The mandible was extracted on day 17, and the tissues were observed with a fluorescence microscope (Leica, M 205 FA, Wetzlar, Germany).

To statistically analyze relative amounts of the regenerated dental pulp tissue at the 14th day, five sections at 150 μm intervals for each tooth from a total of 5 teeth, each transplanted with dental pulp CD105-positive cells with SDF-1, adipose CD105-positive cells with SDF-1, total dental pulp cells with SDF-1, only SDF-1 without cells, only dental pulp CD105-positive cells without SDF-1, and only scaffold without cells were examined. Then, photographs of these samples were taken with a binocular microscopy (Leica, M 205 FA), and analyzed with Leica Application Suite software. The ratio of newly regenerated tissues to the surface area of the root canal was calculated by averaging three positions on each tooth. Statistical analyses were performed using a Student's t-test.

Expressions of dentinsialophosphoprotein (Dspp) and enamelysin, differentiation markers of odontoblast in vivo were observed alignment along the root canal surface by in situ hybridization in 5 μm-paraffin sections 90 days after transplantation of dental pulp CD105-positive cells with SDF-1. Canine cDNA of Dspp (183 bp) and enamelysin (195 bp) were cut with NcoI and Spe I, respectively, and linearized, thereby forming anti-sense probes. The probes were formed from plasmid after subcloning of a PCR product, and obtained from primers shown in Tables 2 and 3 used in real-time RT-PCR. DIG signals were detected with a TSA system (PerkinElmer, Waltham, Mass., USA).

[Dental Pulp Regeneration by Transplantation in Root Canal after Pulpectomy of Dental Pulp CD105-Positive Cells]

Figure 11A:
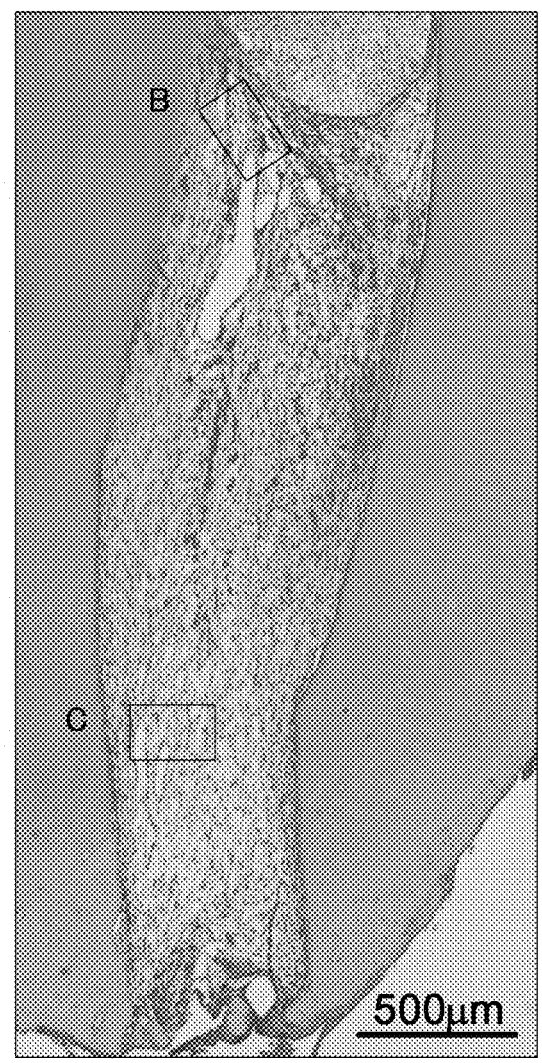
FIG. 11A is a photograph showing dental pulp regeneration 14 days after autologous transplantation of dental pulp CD105-positive cells with SDF-1 into the emptied root canal of a canine tooth.
Figure 11B:
FIG. 11B is a partially magnified photograph showing dental pulp regeneration 14 days after autologous transplantation of dental pulp CD105-positive cells with SDF-1 into the emptied root canal of a canine tooth.
Figure 11C:
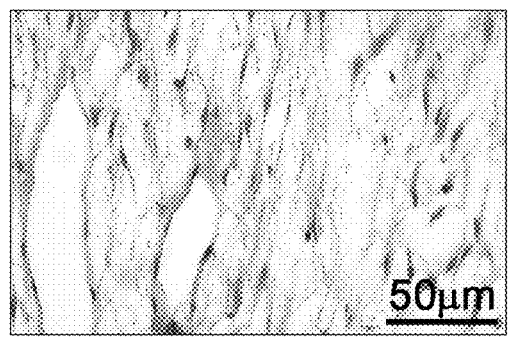
FIG. 11C a partially magnified photograph showing dental pulp regeneration 14 days after autologous transplantation of dental pulp CD105-positive cells with SDF-1 into the emptied root canal of a canine tooth.
Figure 11D:
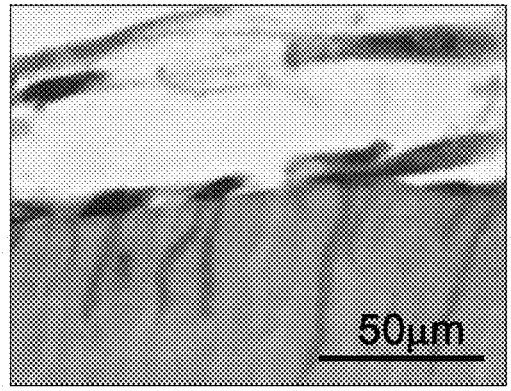
FIG. 11D is a photograph showing odontoblastic differentiation in the regenerated dental pulp tissue 14 days after autologous transplantation of dental pulp CD105-positive cells and SDF-1 into the emptied root canal of a canine tooth.
Figure 11E:
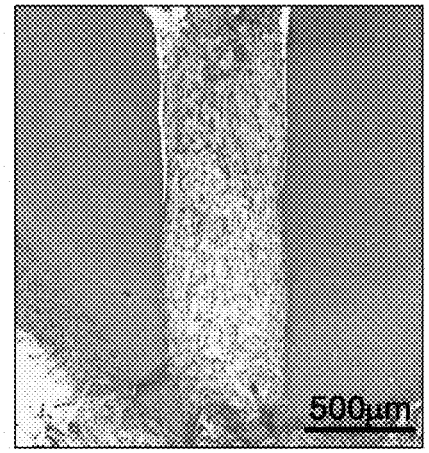
FIG. 11E is a photograph showing dental pulp regeneration 14 days after autologous transplantation of dental pulp CD105-positive cells into the emptied root canal of a canine tooth.
Figure 11F:
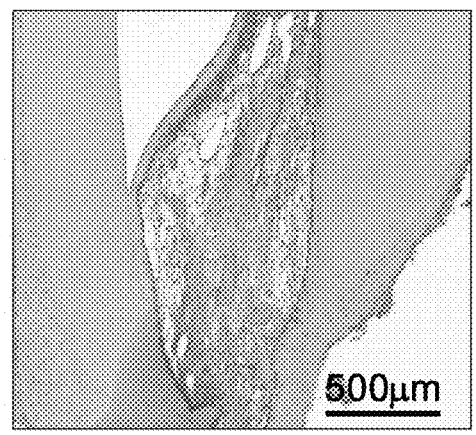
FIG. 11F is a photograph showing dental pulp regeneration 14 days after autologous transplantation of SDF-1 only into the emptied root canal of a canine tooth.
Figure 11G:
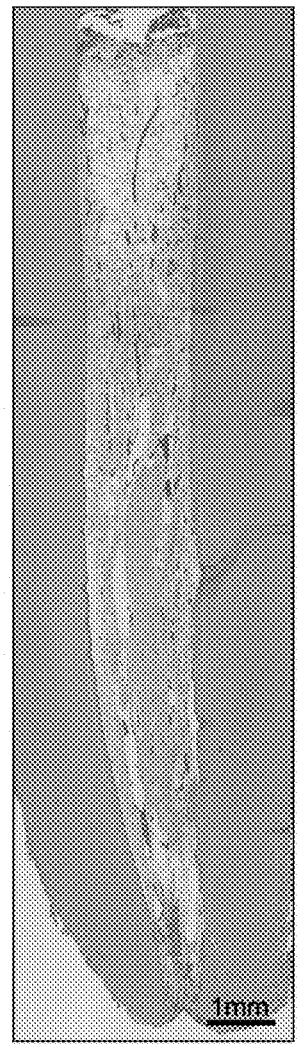
FIG. 11G is a photograph showing dental pulp regeneration 90 days after autologous transplantation of dental pulp CD105-positive cells with SDF-1 into the emptied root canal of a canine tooth.
Figure 11H:
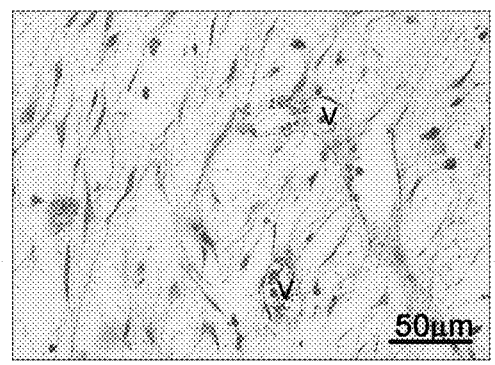
FIG. 11H is a photograph showing dental pulp regeneration 90 days after autologous transplantation of dental pulp CD105-positive cells with SDF-1 into the emptied root canal of a canine tooth, and showing angiogenesis in the upper part of the regenerated tissue.
Figure 11I:
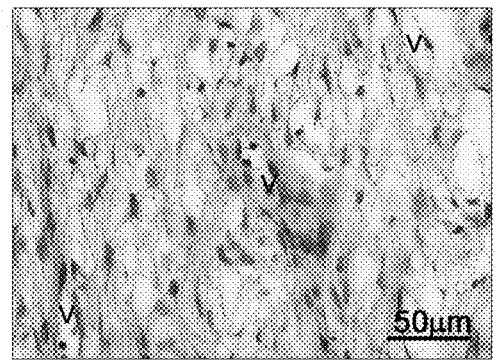
FIG. 11I is a photograph showing dental pulp regeneration 90 days after autologous transplantation of dental pulp CD105-positive cells with SDF-1 into the emptied root canal of a canine tooth, and showing angiogenesis in the middle part of the regenerated tissue.
Figure 11J:
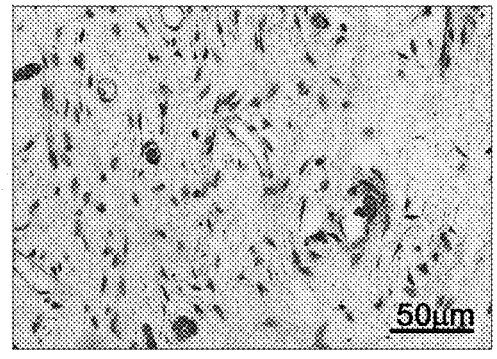
FIG. 11J is a photograph showing cells in normal dental pulp tissues.
Figure 11K:
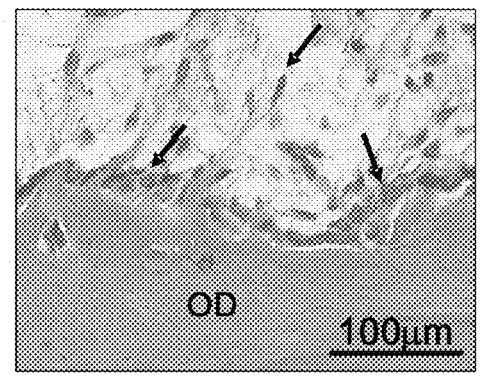
FIG. 11K is a photograph showing odontoblastic layer attached to osteo/tubular dentin (OD) which is newly formed along the dentinal wall on the 90th day after pulpectomy of a canine tooth followed by autologous transplantation of dental pulp CD105-positive cells with SDF-1 into the emptied root canal.
Figure 11L:
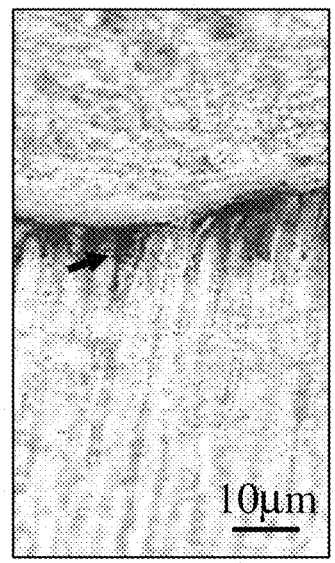
FIG. 11L is a photograph showing odontoblastic differentiation by the in situ hybridization analysis on the 90th day after pulpectomy of a canine tooth and followed by autologous transplantation of dental pulp CD105-positive cells and SDF-1 with expression of Enamelysin/MMP20.
Figure 11M:
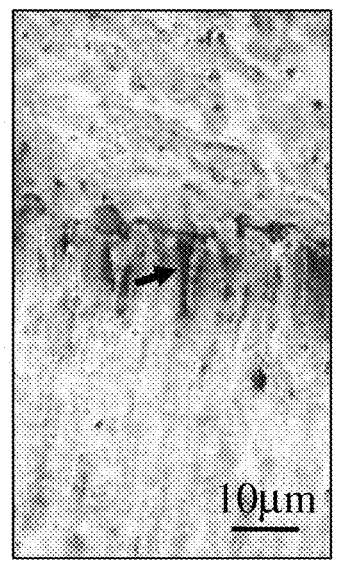
FIG. 11M is a photograph showing odontoblastic differentiation by the in situ hybridization analysis on the 90th day after pulpectomy of a canine tooth and followed by autologous transplantation of dental pulp CD105-positive cells and SDF-1 with expression of Dentin sialophosphoprotein (Dspp).

Then, by the method as described above in FIG. 3, dental pulp CD105-positive cells with SDF-1 were autologously transplanted into the root canal after pulpectomy in a canine permanent tooth with a complete apical closure. FIG. 11A is a photograph showing dental pulp regeneration by transplantation of dental pulp CD105-positive cells with SDF-1. FIG. 11B is a magnified photograph of an area B in FIG. 11A. FIG. 11C is a magnified photograph of an area C in FIG. 11A. As shown in FIGS. 11A, 11B, and 11C, dental pulp CD105-positive cells formed dental pulp-like tissues by day 14 when transplanted with SDF-1. As shown in FIG. 11E, although dental pulp-like tissue was formed by transplantation of only CD105-positive cells, formation of dental pulp-like tissues was further promoted by transplantation of CD105-positive cells with SDF-1. On the other hand, as shown in FIG. 11F, when only SDF-1 was transplanted, only a very small amount of dental pulp was formed. As shown in FIG. 11S, a statistical analysis in a non-paired Student's t test showed that the regenerated area was significantly larger (3.3-fold and 4.2-fold increase) when dental pulp CD105-positive cells were transplanted with SDF-1 compared with only CD105-positive cells or only SDF-1, respectively. As shown in FIG. 11D, odontoblast-like cells attached to the dentinal wall of the root canal, extending their processes into dentinal tubules. As shown in FIG. 11G, dental pulp-like tissues was further extended to the cement-dentinal junction 90 days after transplantation of dental pulp CD105-positive cells with SDF-1. As shown in FIG. 11H, the cells in the upper part of the regenerated tissue were spindle-shaped and, as shown in FIG. 11I, were stellate-like in the middle part. These cells in the regenerated tissues were similar to those in the normal dental pulp tissues shown in FIG. 11J. As shown in FIGS. 11G and 11K, it is notable that tubular dentin was observed along the dentinal wall. As shown in FIGS. 11L and 11M, odontoblasts lining along the dentinal wall were positive for enamelysin/matrix metalloproteinase (MMP) 20 and Dspp, two markers for odontoblasts.

Figure 11N:
FIG. 11N is a photograph showing dental pulp regeneration 14 days after autologous transplantation of total dental pulp cells with SDF-1 into the emptied root canal of a canine tooth.
Figure 11O:
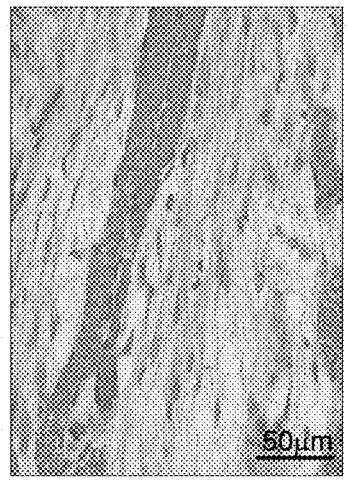
FIG. 11O is a magnified photograph showing dental pulp regeneration 14 days after autologous transplantation of total dental pulp cells with SDF-1 into the emptied root canal of a canine tooth, and showing angiogenesis in the upper part of the regenerated tissue.
Figure 11P:
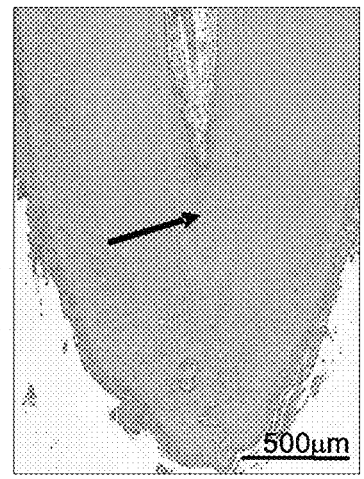
FIG. 11P is a photograph showing showing dental pulp regeneration 90 days after autologous transplantation of total dental pulp cells with SDF-1 into the emptied root canal of a canine tooth.
Figure 11Q:
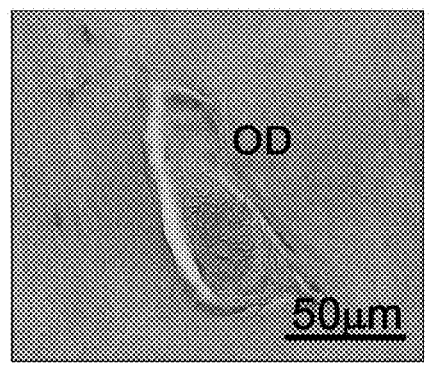
FIG. 11Q is a magnified photograph showing showing dental pulp regeneration 90 days after autologous transplantation of total dental pulp cells with SDF-1 into the emptied root canal of a canine tooth.
Figure 11R:
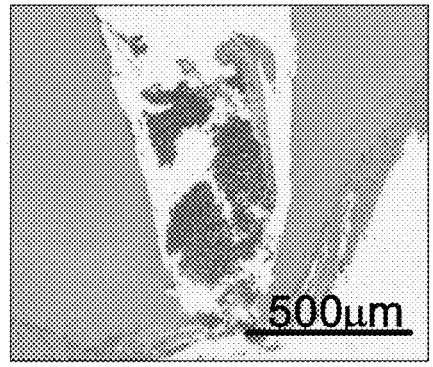
FIG. 11R is a photograph showing showing dental pulp regeneration 14 days after autologous transplantation of adipose CD105-positive cells with SDF-1 into the emptied root canal of a canine tooth.
Figure 11S:
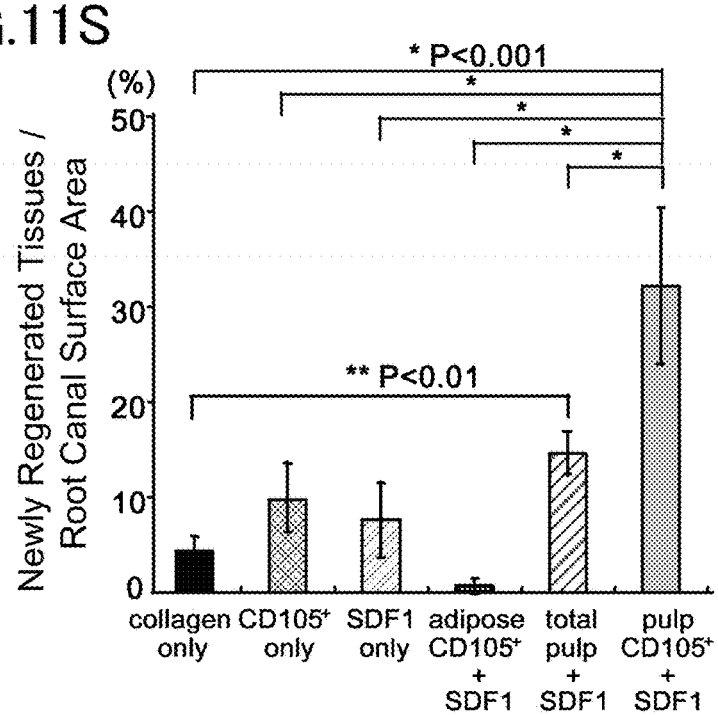
FIG. 11S is a graph showing the ratio of newly regenerated tissues on the 14th day to the root canal surface area where data is represented by the average±SD of five samples.
Figure 11T:
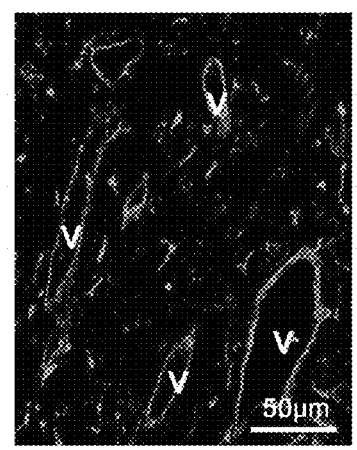
FIG. 11T is a photograph showing immunostaining with BS-1 lectin.
Figure 11U:
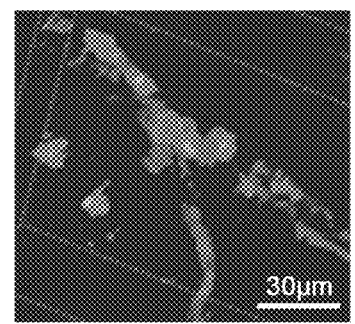
FIG. 11U is a photograph showing a three-dimensional analysis on newly formed blood vessels with whole-mount lectin staining, and shows the presence of transplanted dental pulp CD105-positive cells around newly formed blood capillaries.
Figure 11V:
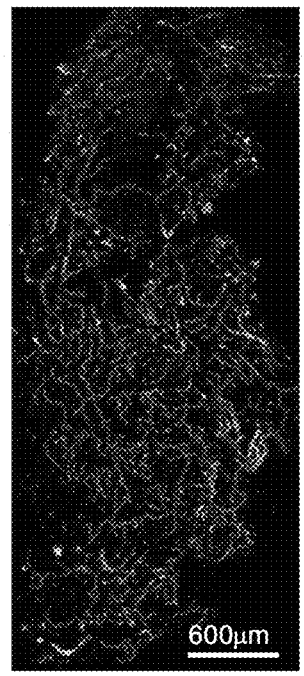
FIG. 11V is a photograph showing a three-dimensional analysis on newly formed blood vessels with whole-mount lectin staining, and a three-dimensional image of induced blood vessels of regenerated tissues on the 14th day.
Figure 11W:
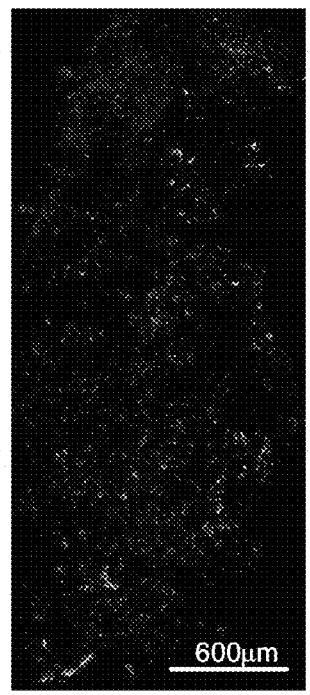
FIG. 11W is a photograph showing a three-dimensional analysis on newly formed blood vessels with whole-mount lectin staining, and shows that transplanted cells labeled with Dil are dispersed in the entire regenerated tissues.
Figure 11X:
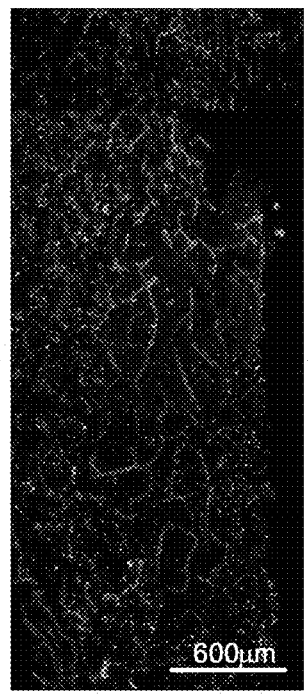
FIG. 11X is a photograph showing normal dental pulp tissues.
Figure 11Y:
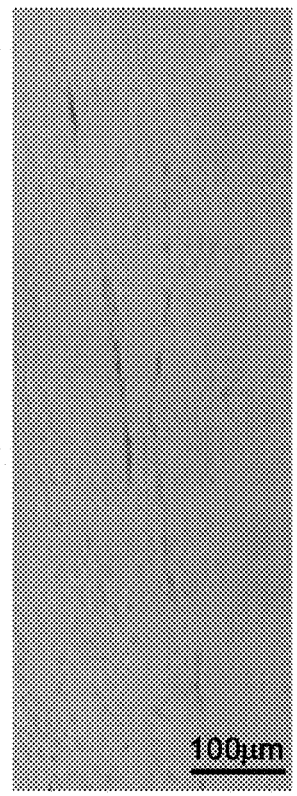
FIG. 11Y is a photograph showing PGP 9.5 immunostaining of newly regenerated tissues on the 14th day.
Figure 11Z:
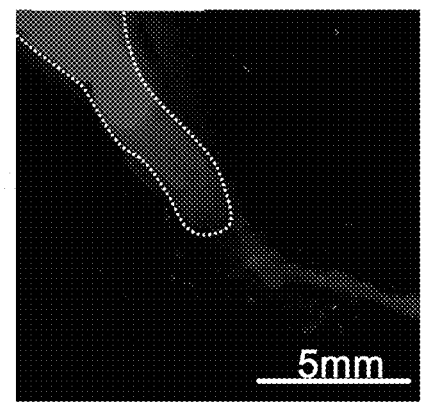
FIG. 11Z is a photograph showing Dil labeling of dental pulp tissues regenerated in the mandibular third incisor.

However, as shown in FIGS. 11N and 11O, in transplantation of unfractionated total dental pulp cells instead of CD105-positive cells, only a smaller amount of dental pulp tissues were regenerated. Calcification such as calcified tissues indicated by the arrow in FIG. 11P and osteodentin indicated as OD in FIG. 11Q was observed after 90 days. Likewise, as shown in FIG. 11R, in transplantation of CD105-positive cells derived from adipose tissues, only a small amount of regenerated tissues was observed. As shown in FIG. 11S, a further statistical analysis showed that in transplantation of dental pulp CD105-positive cells with SDF-1, the ratio of newly regenerated tissues to the surface areas of the root canal on day 14 was significantly higher (51.6 times and 2.2 times, respectively) than those in transplantation of adipose CD105-positive cells with SDF-1 and in transplantation of total dental pulp cells with SDF-1. As shown in FIG. 11T, frozen sections were stained with BS-1 lectin, and analyzed with a confocal laser microscope. Angiogenesis was observed in the regenerated tissues. As shown in FIG. 11U, with a two-photon microscope analysis, numerous DiI-labeled transplanted pulp CD105-positive cells were observed in the vicinity of the newly formed blood capillaries, implicating a trophic role for these cells to release angiogenic factors in neovascularization. As shown in FIG. 11V, a three-dimensional image of induced vascularization in the regenerated tissues on day 14 was similar in density and orientation to that in the normal dental pulp shown in FIG. 11X. As shown in FIG. 11W, transplanted CD105-positive cells were observed everywhere in newly regenerated dental pulp, and dental pulp CD105-positive cells were suggested to have migration ability in an upper part thereof by SDF-1. As shown in FIG. 11Y, neuronal process stained by PGP 9.5 antibodies extended from the apical foramen into the newly regenerated tissue. As shown in FIG. 11Z, DiI labeling on the regenerated pulp in the mandibular third incisor showed that the neuronal process from the regenerated pulp (indicated by the dotted line) connecting to inferior alveolar nerves.

[Two-Dimensional Electrophoresis Analysis and Gene Expression Analysis in Dental Pulp Regeneration]

For a two-dimensional electrophoresis analysis of regenerated tissues, regenerated dental pulp-like tissues, normal dental pulp tissues, and periodontium tissues on day 28 were minced into pieces, and were dissolved in a lysis buffer (6M urea, 1.97M thiourea, 2% (w/v) CHAPS, 64.8 mM DTT, 2% (v/v) Pharmalyte), and subjected to ultrasound. Then, the resultant samples were centrifuged at 15,000 rpm for 15 minutes at 4° C., and two-dimensional electrophoresis was performed on the supernatant. Isoelectric focusing (IEF) was performed on a CoolPhoreSter2-DE system. IPG strips (Immobiline DryStrips, pH 4 to 7, 18 cm, GE) were used according to an instruction of the manufacturer. The IPG strips were hydrated again in a rehydration solution (6M urea, 1.97 M thiourea, 2% (v/v) Triton X-100, 13 mM DTT, 2% (v/v) Pharmalyte, 2.5 mM acetic acid, 0.0025% BPB) overnight at 20° C. The isoelectric focusing (IEF) was performed with the voltage gradually increased with 500V for two hours, 700-3000 V for one hour, and 3500V for 24 hours. After the isoelectric focusing, the IPG strips were caused to react in an equilibration buffer (6 M urea, 2.4 mM DTT, 5 mM Tris-HCl, pH 6.8, 2% (w/v) SDS, 0.0025% BPB, 30% (v/v) Glycerol) for 30 minutes at room temperature. The IPG strips were further equilibrated in 5 mM Tris-HCl, pH 6.8, 2% (w/v) SDS, 0.0025% BPB, 30% (v/v) Glycerol, 243 mM iodoacetamid for 20 minutes at room temperature. Thereafter, in the second dimension, proteins were migrated in 12.5% SDS-PAGE gel (20 cm×20 cm) with 25 mA/gel for 15 minutes and then 30 mA/gel. The gel was stained with Flamingo Fluorescent Gel Stain (Bio-Rad Laboratories, CA, USA), and scanned with a FluoroPhorester 3000 (Anatech, Tokyo, Japan). The gel image was analyzed with a progenesis (Nonlinear Dynamics, NC, USA), and patterns of the gel were compared with one another.

Real-time RT-PCR analyses were performed using canine axin2, periostin, and asporin/periodontium-associated protein 1 (PLAP-1) specific to a periodontium. Expression of collagen type αI (I), syndecan3, and tenascin C in the regenerated tissues was compared with those in normal dental pulp and a periodontium.

[Protein Chemical Analyses and Gene Expression Analysis by Two-Dimensional Electrophoreses of Regenerated Dental Pulp]

Figure 12A:
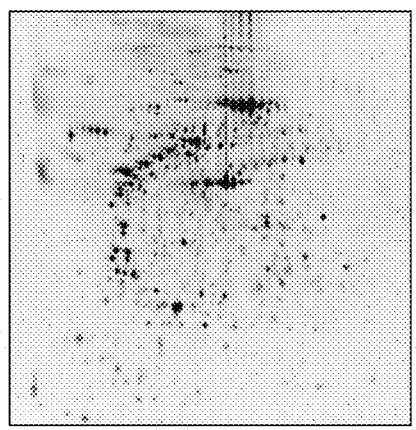
FIG. 12A is a photograph showing two-dimensional electrophoresis of normal dental pulp tissues.
Figure 12B:
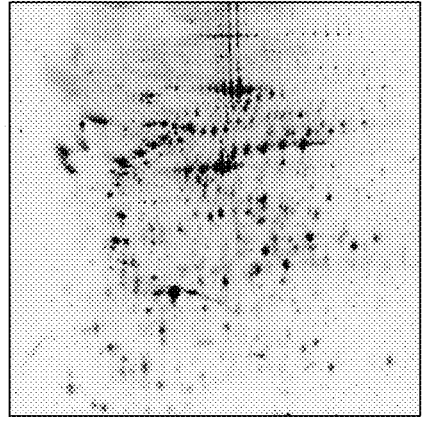
FIG. 12B is a photograph showing two-dimensional electrophoresis of regenerated dental pulp tissues.
Figure 12C:
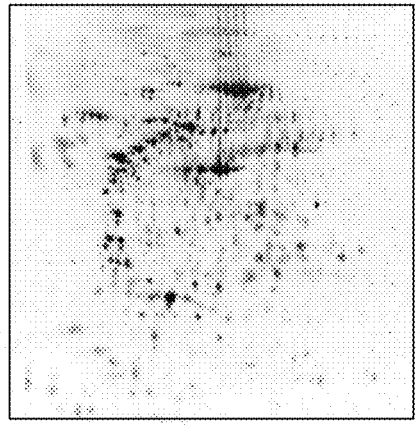
FIG. 12C is a photograph in which two-dimensional electrophoresis of normal dental pulp tissues and two-dimensional electrophoresis of regenerated dental pulp tissues are overlaid on each other.
Figure 12D:
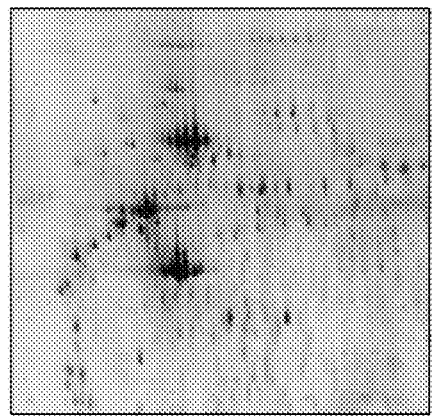
FIG. 12D is a photograph showing two-dimensional electrophoresis of normal dental pulp tissues.
Figure 12E:
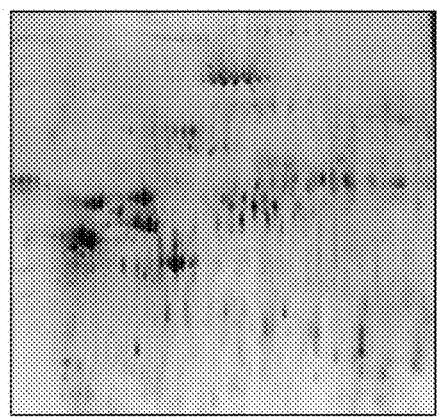
FIG. 12E is a photograph showing two-dimensional electrophoresis of periodontium tissues.
Figure 12F:
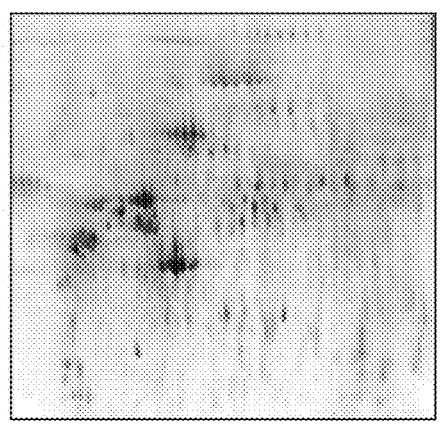
FIG. 12F is a photograph in which two-dimensional electrophoresis of normal dental pulp tissues and two-dimensional electrophoresis of periodontium tissues are overlaid on each other.

As shown in FIGS. 12A, 12B, and 12C, two-dimensional electrophoresis analyses demonstrated that the protein expression pattern of the regenerated dental pulp tissues was qualitatively and quantatively similar to that of the normal dental pulp tissues of the same individual on the 28th day. The protein spots detected both in the normal and regenerated dental pulp tissues represented 85.5% (i.e., 123 spots). On the other hand, as shown in FIGS. 12D, 12E, and 12F, there were some differences in the protein spots of the normal dental pulp tissues compared with periodontal ligament. Accordingly, the two-dimensional electrophoresis analysis indicates that that the regenerated tissue is identical to true functional normal dental pulp.

A marker specific to dental pulp tissues has not been found yet. Thus, to prove that the regenerated tissues are normal dental pulp tissues, axin2, periostin, and asporin/periodontium-associated protein 1 (PLAP-1) were additionally used as markers specific to periodontal ligament tissues. Expression of Axin2, periostin, and PLAP-1 mRNA in normal periodontal tissues was 25,531 times, 179 times, and 11 times higher, respectively, than that in the regenerated dental pulp tissues on the 28th day. As shown in Table 6, expression of these genes in the normal dental pulp were almost the same (0.4, 0.4, and 2.4 times, respectively) as that in the regenerated tissues.

TABLE 6

| | Normal dental pulp/regenerated dental pulp tissues | Normal periodontium/ regenerated dental pulp tissues |
|---|---|---|
| Axin2 | 0.4 | 25531.7 |
| Periostin | 0.4 | 178.5 |
| PLAP-1 | 2.4 | 11.2 |
| Tenascin C | 1.0 | 0.01 |
| Syndecan 3 | 2.0 | 0.07 |
| collagenα1(I) | 2.3 | 9.3 |

As shown in Table 6, collagen αI (I) was 9.3 times more expressed in periodontal ligament compared with that in regenerated tissues, and no significant difference was observed between normal dental pulp and regenerated dental pulp. Syndecan 3 and Tenascin C, known to be highly expressed in dental pulp, were 14.3 times and 50.0 times more expressed in regenerated tissues, respectively, compared with periodontal ligament. Accordingly, a two-dimensional electrophoresis analysis and a gene expression analysis indicate that that the regenerated tissue is identical to true functional normal dental pulp.

[Dental Pulp Regeneration by Autologous Transplantation of Dental Pulp CD105-Positive Cells in Root Canal after Infected Root Canal Treatment]

Dental pulp was completely removed from a canine permanent tooth with a complete apical closure, and the apical foramen was enlarged to #30 with a K-file. Then, the root canal was left open for two weeks. In this manner, an experimental tooth model for infected root canal was produced. Thereafter, the model was cleaned with sodium hypochlorite and oxydol alternately used. Subsequently, Smearclean was placed in the root canal for 30 seconds, and then the root canal was further cleaned with physiologic saline. Thereafter, the root canal was medicated with formocresol (FC) for one week to be sterilized. Subsequently, the root canal was cleaned again with physiologic saline, and the inside of the root canal was dried with a paper point. A root canal filler in which dental pulp stem cells were transplanted to the apical part, and SDF-1 were transplanted to the crown part using collagen XYZ as an extracellular matrix. Specifically, in the same manner as autologous transplantation in the root canal after pulpectomy, $1 \times 10^6$ dental pulp CD105-positive cells at the third to fourth passages of culture and collagen XYZ were autologously transplanted in the lower part of the root canal. SDF-1 with a final concentration of 15 ng/ml and collagen XYZ were further transplanted into the upper part of the root canal, and the cavity was sealed with zinc phosphate cement and composite resin. On day 14, a sample was prepared. This sample was morphologically observed by a common procedure.

Figure 13A:
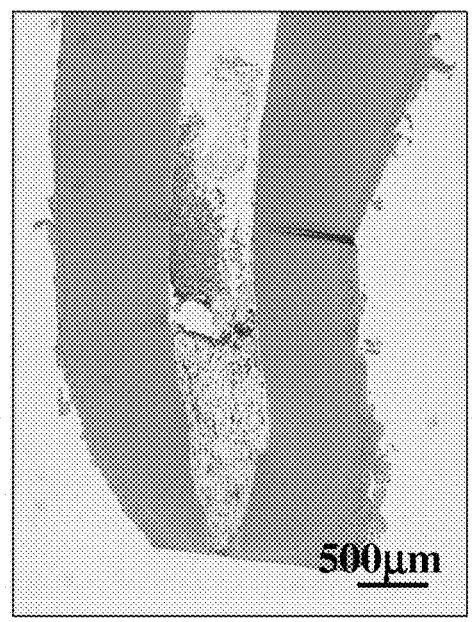
FIG. 13A is a photograph showing dental pulp regeneration on the 14th day after root canal treatment of a canine infected tooth and autologous transplantation of dental pulp CD105-positive cells with SDF-1 into the root canal of an extracted tooth.
Figure 13B:
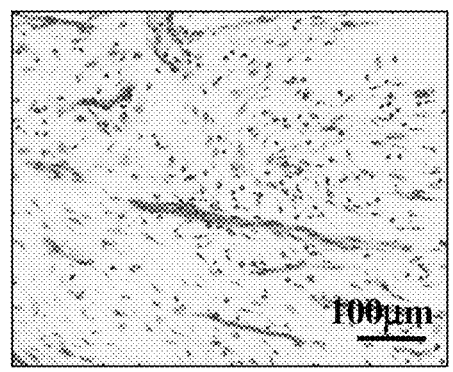
FIG. 13B is a photograph showing dental pulp regeneration on the 14th day after root canal treatment of a canine infected tooth and autologous transplantation of dental pulp CD105-positive cells with SDF-1 into the root canal of an unextracted tooth.
Figure 13C:
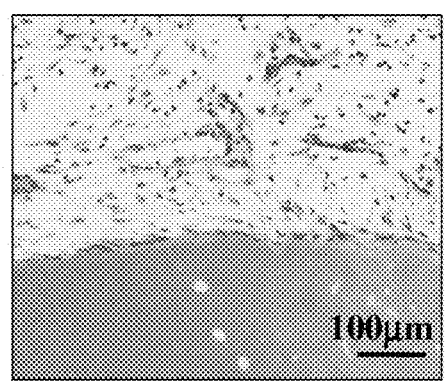
FIG. 13C is a partially magnified photograph showing dental pulp regeneration on the 14th day after root canal treatment of a canine infected tooth and autologous transplantation of dental pulp CD105-positive cells with SDF-1 into the root canal of an unextracted tooth.

FIG. 13A is a photograph showing dental pulp regeneration with SDF-1 and dental pulp CD105-positive cells. FIG. 13B is a magnified photograph showing the middle part of dental pulp tissues regenerated in the root canal in FIG. 13A. FIG. 13C is a magnified photograph showing a portion of dental pulp tissues regenerated in the root canal in FIG. 13A in contact with the dentinal wall. As shown in FIGS. 13A, 13B, and 13C, dental pulp-like tissues were formed by day 13 when dental pulp CD105-positive cells were transplanted together with SDF-1. As shown in FIG. 13B, in dental pulp tissues, new blood vessels were regenerated, and dental pulp cells were observed, but a small amount of inflammatory cells were also dispersed. As shown in FIG. 13C, odontoblast-like cells were attached along the dentinal wall of the root canal, and were lined in a layer.

Third Example

Then, in a third example, a comparison was made between the case of filling a root canal with extraction and the case of filling a root canal without extraction, using a chemotactic factor G-CSF and dental pulp CD105-positive cells.

Figure 14A:
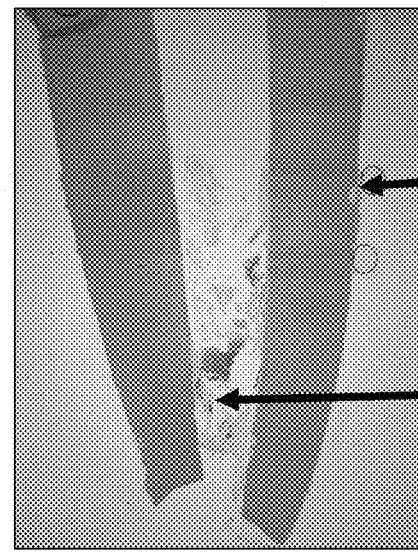
FIG. 14A is a photograph showing dental pulp regeneration on the 14th day after root canal treatment of a canine infected tooth and autologous transplantation of dental pulp CD105-positive cells with G-CSF into the root canal of an extracted tooth.

In the same manner as in the first and second examples described above, after a canine anterior tooth has been extracted, $5 \times 10^5$ (10 μl) of dental pulp CD105-positive cells and collagen XYZ as a scaffold were transplanted into the lower part of the root canal, and 200 ng (10 μl) of G-CSF as a chemotactic factor was transplanted into the upper part of the root canal. The resultant tooth was left for 14 days. FIG. 14A shows the results. As shown in FIG. 14A, only a small amount of dental pulp-like tissues were formed, and as indicated by the arrows, a high inflammation image and external resorption were observed.

Figure 14B:
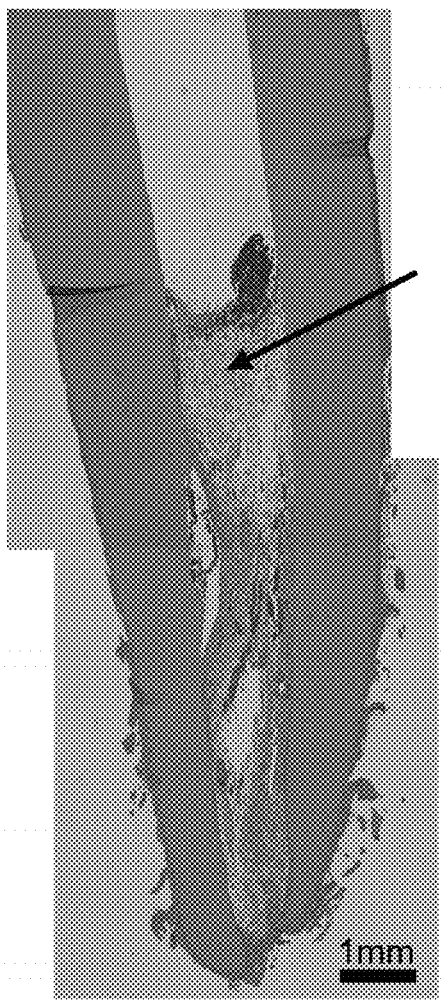
FIG. 14B is a photograph showing dental pulp regeneration on the 14th day after root canal treatment of a canine infected tooth and autologous transplantation of dental pulp CD105-positive cells with G-CSF into the root canal of an unextracted tooth.
Figure 14C:
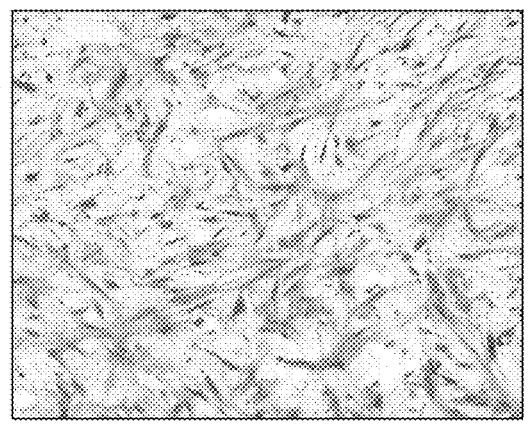
FIG. 14C is a partially magnified photograph showing dental pulp regeneration on the 14th day after root canal treatment of a canine infected tooth and autologous transplantation of dental pulp CD105-positive cells with G-CSF into the root canal of an unextracted tooth.

Then, without extraction of a canine anterior tooth, $5\times10^5$ (10 μl) of dental pulp CD105-positive cells and collagen XYZ as a scaffold were transplanted into a lower part of the root canal, and 200 ng (10 μl) of G-CSF as a chemotactic factor was transplanted into an upper part of the root canal. The resultant tooth was left for 14 days. FIG. 14B shows the results. As shown in FIG. 14B, a higher amount of dental pulp-like tissue was formed, and no inflammation images were observed. No external resorption was observed, either. FIG. 14C is a magnified photograph showing a portion of dental pulp-like tissues indicated by the arrow in FIG. 14B. As shown in FIG. 14C, slender spindle-shaped fibroblast-like dental pulp cells were present in regenerated dental pulp-like tissues, and no inflammatory cells were observed.

DESCRIPTION OF REFERENCE CHARACTERS 100 target tooth
110 periapical periodontitis
200 unextracted tooth root canal filler
210 extracellular matrix
220 dental pulp stem cells
230 chemotactic factor
400 blood vessel
500 dentin
610 gelatin
620 resin
630 morphogen

SEQUENCE LISTING FREE TEXT

SEQ ID NOs 1-64: primer

The invention claimed is:

1. A dental tissue regeneration method without tooth extraction, the method comprising:
performing a pulpectomy or enlargement and cleaning of an infected root canal on an unextracted tooth;
transplanting an unextracted tooth root canal filler into an apical part of the root canal; and
regenerating a dental tissue in the root canal,
wherein the unextracted tooth root canal filler comprises:
(a) CD105-positive and CD146-negative dental pulp cells, or
(b) CXCR4-positive dental pulp stem cells, and
(c) an extracellular matrix,
and wherein the unextracted tooth root canal filler does not comprise stromal cell-derived factor-1 (SDF1).

2. The dental tissue regeneration method of claim 1, wherein in the unextracted tooth root canal filler, the dental pulp stem cells are transplanted to the apical part of the root canal, and a chemotactic factor comprising at least one factor selected from the group consisting of a cell chemotactic factor, a cell growth factor, a neurotrophic factor, and an angiogenic factor is transplanted to a tooth crown part of the root canal.

3. The dental tissue regeneration method of claim 2, wherein the cell chemotactic factor is at least one cell chemotactic factor selected from the group consisting of VEGF, G-CSF, SCF, MMP3, Slit, and GM-CSF.

4. The dental tissue regeneration method of claim 2, wherein the cell growth factor is at least one cell growth factor selected from the group consisting of IGF, bFGF, and PDGF.

5. The dental tissue regeneration method of claim 2, wherein the neurotrophic factor is at least one neurotrophic factor selected from the group consisting of GDNF, BDNF, NGF, Neuropeptide Y, and Neurotrophin 3.

6. The dental tissue regeneration method of claim 1, wherein the extracellular matrix is made of biocompatible materials containing at least one biocompatible material selected from the group consisting of collagen, synthetic proteoglycans, gelatin, hydrogel, fibrin, phosphophorin, heparan sulfate, heparin, laminin, fibronectin, alginic acid, hyaluronic acid, chitin, PLA, PLGA, PEG, PGA, PDLLA, PCL, hydroxyapatite, β-TCP, calcium carbonate, titanium, and gold.

7. The dental tissue regeneration method of claim 1, wherein the root canal is enlarged before transplantation of the root canal filler into the apical part of the root canal, thereby enlarging the apical part of the root canal to a predetermined size.

8. The dental tissue regeneration method of claim 1, wherein a concentration of the dental pulp stem cells in the extracellular matrix is in the range from $1\times10^3$ cells/μl to $1\times10^6$ cells/μl, both inclusive.

* * * * *

UNITED STATES PATENT AND TRADEMARK OFFICE
CERTIFICATE OF CORRECTION

PATENT NO. : 9,724,368 B2
APPLICATION NO. : 14/102295
DATED : August 8, 2017
INVENTOR(S) : Nakashima et al.

Page 1 of 2

It is certified that error appears in the above-identified patent and that said Letters Patent is hereby corrected as shown below:

On the Title Page

In Column 2 (page 2, item (56)) at Line 42, under Other Publications, change "Lippincottt" to --Lippincott--.

In Column 2 (page 2, item (56)) at Line 63, under Other Publications, change "regenartion"," to --regeneration",--.

In Column 1 (page 3, item (56)) at Line 3, under Other Publications, change "pithelial" to --epithelial--.

In the Specification

In Column 2 at Line 34, change "pancreata" to --pancreas--.

In Column 3 at Line 24, change "transplantion" to --transplantation--.

In Column 5 at Line 17, change "Spongel" to --Sponge--.

In Column 8 at Line 6, change "showing showing" to --showing--.

In Column 8 at Line 10 (approx.), change "showing showing" to --showing--.

In Column 8 at Line 15 (approx.), change "showing showing" to --showing--.

In Column 10 at Line 45, change "(glucosaminoglycans)" to --(glycosaminoglycans)--.

In Column 13 at Line 59, change "0.1 ng/µl" to --0.1 ng/µl--.

In Column 21 at Line 41, change "rhombotin 2," to --rhombotin-2,--.

Signed and Sealed this
Eleventh Day of June, 2019

Andrei Iancu
*Director of the United States Patent and Trademark Office*

CERTIFICATE OF CORRECTION (continued)
U.S. Pat. No. 9,724,368 B2

In Column 21 at Line 60, after "450 nm" insert --.--.

In Column 24 at Line 38, change "(Nakarai" to --(Nacalai--.

In Column 24 at Line 56, change "lecitin." to --lecithin.--.

In Column 25 at Line 31, change "Spe I," to --SpeI,--.

In Column 25 at Lines 65-66, change "cementdentinal" to --cementodentinal--.

In Column 27 at Line 8, change "iodoacetamid" to --iodoacetamide--.

In Column 27 at Line 39, change "that that" to --that--.

In Column 27 at Line 65, change "αI (I)" to --α1 (I)--.

In Column 28 at Line 7, change "that that" to --that--.

```
                        SEQUENCE LISTING

<160> NUMBER OF SEQ ID NOS: 64

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ctgtggcaaa ctggtacttc                                              20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tcaacaggag ggcaggtatc                                              20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
agctagtctc caagcgacga                                              20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ccacgtttgc aactgtccta                                              20

<210> SEQ ID NO 5
<211> LENGTH: 20
<212> TYPE: DNA
```

```
<213> ORGANISM: Artificial Sequence
<220> FEATURE:
<223> OTHER INFORMATION: Primer

<400> SEQUENCE: 5
gtggtgacgg agaagcaaca                                                 20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ttctgtctgg tcaccgactg                                                 20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cactcccgtt cagtctcctc                                                 20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ccagatgaag ttgctgacga                                                 20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tggacacgtc cgtgctcttc                                                 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ctcggatctt ccagatcacc                                                 20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ccctctgatt cctccaatga                                                 20
```

```
<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ggatggccaa aatgaagaga                                                    20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ctacctccac catgccaagt                                                    20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
acgcaggatg gcttgaagat                                                    20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gcagaacctg cttttcttgg                                                    20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ccctcagggt caaacacttc                                                    20

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
gccatgaacg ccaaggtc                                                      18

<210> SEQ ID NO 18
<211> LENGTH: 24
<212> TYPE: DNA
<213> ORGANISM: Artificial Sequence
<220> FEATURE:
```

<223> OTHER INFORMATION: Primer

<400> SEQUENCE: 18
cttgttttag agctttctcc aggt                                        24

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
caacaggact cacaggagca                                             20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
atgttcacct ctcccagcac                                             20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gttggccgac acttttgaac                                             20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cctcatcgac atgtttgcag                                             20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
atcaccaggc agaggtatgg                                             20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ttgggaggat aggcagattc                                             20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cccctcccct tgtatctcat                                           20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
cgtaggtttg ggacgttttg                                           20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
gtatgtgcgt ttgcatgtcc                                           20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
caggagccag aggagaaatg                                           20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
gggattaacc aggctggaat                                           20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tgtctcccgt ctctgctttt                                           20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ggcgcctcta ctacaagctg                                         20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
tatctgtcgc ccacacagaa                                         20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
ccccaggtgt tatcagcttc                                         20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
tctttctctc cgttggctgt                                         20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
cacgtccttg gtcgatcttt                                         20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
agaatgcaac ccacaaaagg                                         20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
cggatgacag aaaagtcaag                                         20

<210> SEQ ID NO 38
<211> LENGTH: 20

```
<212> TYPE: DNA
<213> ORGANISM: Artificial Sequence
<220> FEATURE:
<223> OTHER INFORMATION: Primer

<400> SEQUENCE: 38
ttcagcttga tgtcccttgg                                              20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
gctggaccga ctatcagagg                                              20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
ctggtaggat gcgatgtcag                                              20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
acaagatggc atcaaaccag                                              20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
cttcttctcc aggccatcag                                              20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
tattcaccgt tgctgctcac                                              20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
```
tacaatgcct ggatccctttt                                              20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
ggcagcgagg tggtgaggag                                               20

<210> SEQ ID NO 46
<211> LENGTH: 19
<212> TYPE: DNA
<213> ORGANISM: Artificial Sequence
<220> FEATURE:
<223> OTHER INFORMATION: Primer

<400> SEQUENCE: 46
ctagaccggg ccatagaag                                                19

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
gtcctagtgg gaatggagca                                               20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
tcttcagggc catcatcttc                                               20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
gaaagggtca ggtcaccaaa                                               20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
catttgtccc tctccaggaa                                               20

<210> SEQ ID NO 51
<211> LENGTH: 20
<212> TYPE: DNA
<213> ORGANISM: Artificial Sequence -continued
<220> FEATURE:
<223> OTHER INFORMATION: Primer

<400> SEQUENCE: 51
aaaccattgg aggcaaacag                                              20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tgcagcttca agtaggctga                                              20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
tcccgtcagg attacaggag                                              20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
gaacgctcat tctgctcaca                                              20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
tggctgtctt ggacacagag                                              20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
gactccagag ttggggtctg                                              20

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
tcatgcagga cagcttcaac                                              20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
agggctggaa tctagggaaa                                                    20

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
cttcctggaa tgaagggaca                                                    20

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
cagtagcacc atcgtttcca                                                    20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
agggtcctgc tggaaagaat                                                    20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
ggaactccag gtgaaccaga                                                    20

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
aagtacccca ttgagcacgg                                                    20

<210> SEQ ID NO 64
<211> LENGTH: 20
<212> TYPE: DNA
<213> ORGANISM: Artificial Sequence
<220> FEATURE:
<223> OTHER INFORMATION: Primer

```
<400> SEQUENCE: 64
atcacgatgc cagtggtgcg                                               20
```